(12) United States Patent
Patnaik et al.

(10) Patent No.: US 9,110,748 B2
(45) Date of Patent: Aug. 18, 2015

(54) APPARATUS SYSTEM AND METHOD OF DEPICTING PLUME ARRIVAL TIMES

(71) Applicants: Gopal Patnaik, Silver Spring, MD (US); Keith Stephen Obenschain, Burk, VA (US); Adam Joseph Moses, Falls Church, VA (US); Jay Paul Boris, Falls Church, VA (US)

(72) Inventors: Gopal Patnaik, Silver Spring, MD (US); Keith Stephen Obenschain, Burk, VA (US); Adam Joseph Moses, Falls Church, VA (US); Jay Paul Boris, Falls Church, VA (US)

(73) Assignee: The Government of The United States of America, as represented by the Secretary of the Navy, Washington, DC (US)

( * ) Notice: Subject to any disclaimer, the term of this patent is extended or adjusted under 35 U.S.C. 154(b) by 335 days.

(21) Appl. No.: 13/629,842

(22) Filed: Sep. 28, 2012

(65) Prior Publication Data
US 2014/0095123 A1 Apr. 3, 2014

(51) Int. Cl.
*G06G 7/48* (2006.01)
*G06F 7/60* (2006.01)
*G01N 21/94* (2006.01)
*G01N 33/00* (2006.01)
*G01N 15/00* (2006.01)

(52) U.S. Cl.
CPC *G06F 7/60* (2013.01); *G01N 21/94* (2013.01); *G01N 33/00* (2013.01); *G01N 33/0075* (2013.01); *G01N 2015/0088* (2013.01)

(58) Field of Classification Search
CPC ....... G08B 21/12; G06F 2217/16; G06F 9/45; G06F 17/30; G06F 17/00; G06F 19/00; G08N 21/00; G08N 23/00; G08N 29/00; G01N 7/00; G01N 33/00; G01P 5/00
See application file for complete search history.

(56) References Cited

U.S. PATENT DOCUMENTS

| 5,648,914 | A | * | 7/1997 | Bauer et al. | 702/19 |
| 7,542,884 | B2 | | 6/2009 | Boris et al. | |
| 8,614,633 | B1 | * | 12/2013 | Lear et al. | 340/984 |
| 2002/0084900 | A1 | * | 7/2002 | Peterson et al. | 340/573.1 |
| 2004/0204915 | A1 | * | 10/2004 | Steinthal et al. | 702/188 |
| 2006/0187017 | A1 | * | 8/2006 | Kulesz et al. | 340/506 |

(Continued)

OTHER PUBLICATIONS

Boris et al., Fast and accurate prediction of windborne contaminant plumes for civil defense in cities, (CWE2010) Chapel Hill, North Carolina, USA May 23-27, 2010.*

(Continued)

*Primary Examiner* — Kandasamy Thangavelu
(74) *Attorney, Agent, or Firm* — US Naval Research Laboratory; Suresh Koshy; John Leonard Young

(57) ABSTRACT

Computer implemented methods and systems work cooperatively to calculate and display plume arrival time of a CBR contaminant and to alert responders to take action, associated with mitigating the CBR contaminant. The methods and systems comprise: performing, plume arrival time operational use routines, including: sensing an unknown CBR contaminant released in a geographic area of interest and then, over a communications network, alerting and causing responders to mitigate the CBR contaminant by displaying realtime graphics on handheld computer implemented graphics devices, as well as host computers and distributed computers, showing current and predicted paths of plumes of the CBR plume, by estimating an initial source location of the unknown contaminant, calculating and displaying on graphic displays, an arrival time of at least one or more plumes associated with the CBR contaminant.

8 Claims, 19 Drawing Sheets

(56) References Cited

U.S. PATENT DOCUMENTS

| | | | |
|---|---|---|---|
| 2007/0038383 A1* | 2/2007 | Boris et al. | 702/19 |
| 2009/0113990 A1* | 5/2009 | Groves | 73/31.01 |
| 2010/0094565 A1* | 4/2010 | Prince et al. | 702/22 |
| 2010/0332210 A1* | 12/2010 | Birdwell et al. | 703/22 |
| 2011/0063116 A1* | 3/2011 | Lepley et al. | 340/605 |
| 2013/0063300 A1* | 3/2013 | O'Regan et al. | 342/357.25 |

OTHER PUBLICATIONS

Obenschain et al., Use of the NRL DHPI System to Transfer Dispersion Nomograf Capabilities to the Field, 2010 DoD High Performance Computing Modernization Program Users Group Conference.*

Patnaik et al., Fast and Accurate CBR Defense for Homeland Security: Bringing HPC to the First Responder and Warfighter, DoD High Performance Computing Modernization Program Users Group Conference, 2007.*

Wikipedia contributors, "Array data structure," Wikipedia, The Free Encyclopedia, Dec. 3, 2014.*

Boris J.P., "Dust in the Wind: Challenges for urban aerodynamics", 35th AIAA Fluid Dynamics Conference, Jun. 2005.*

J. Boris et al. The How and Why of Nomografs for CT-Analyst, NRL/MR/6440-11-9326, May 3, 2011, pp. 1-15, Naval Research Laboratory, Washington, DC, USA.

* cited by examiner

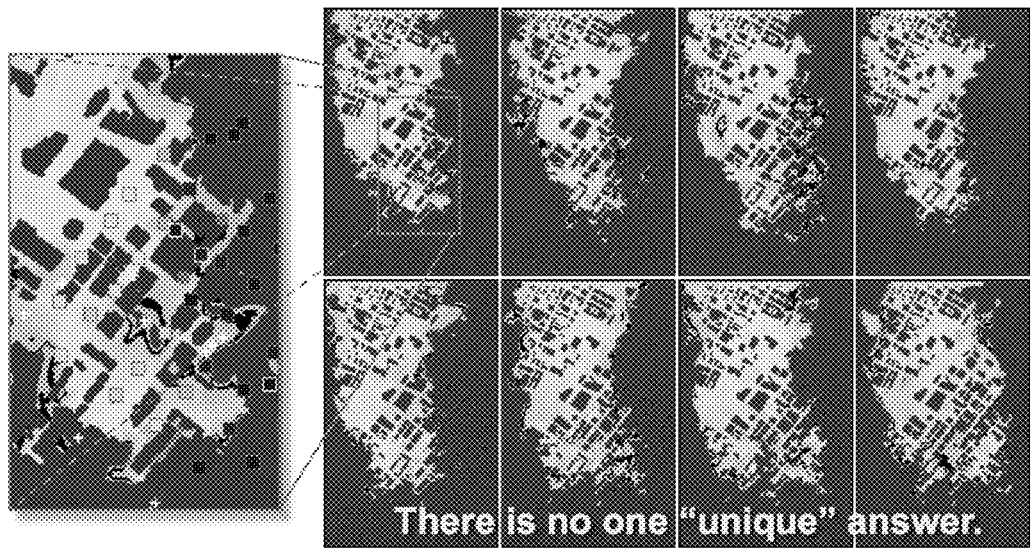
FIG. 10A Having Source 1   FIG. 10B Having Source 2   FIG. 10C Having Source 3   FIG. 10D Having Source 4
FIG. 10L Having Source 1   FIG. 10E Having Source 5   FIG. 10F Having Source 6   FIG. 10G Having Source 7   FIG. 10H Having Source 8

FIG. 11B
FIG. 11C
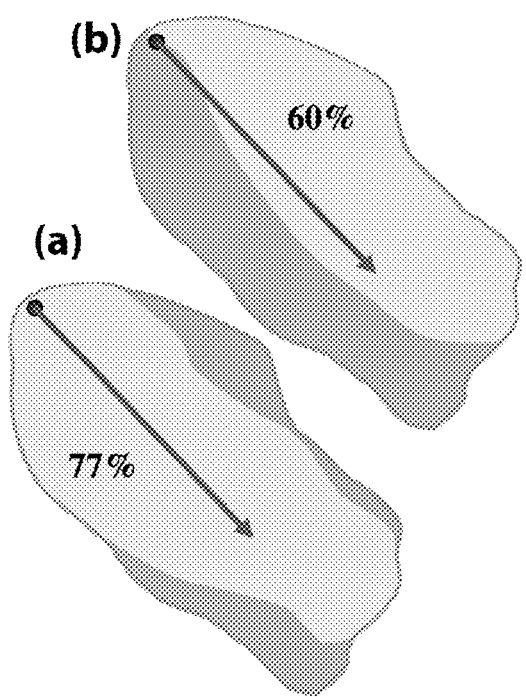
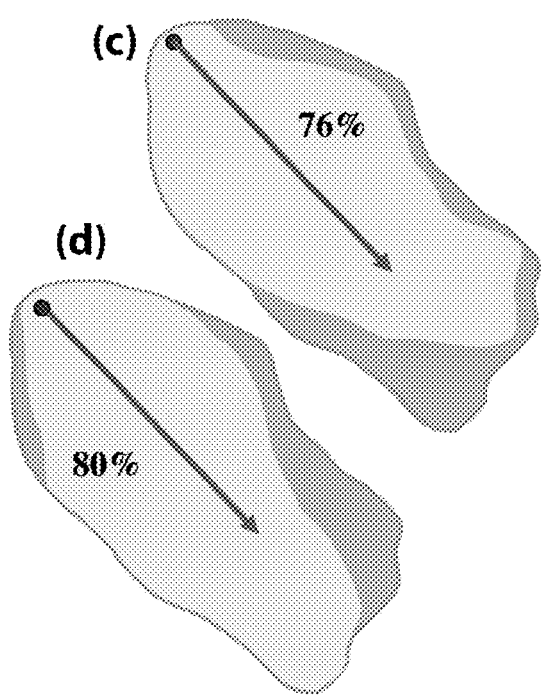
FIG. 11A
FIG. 11D

Nomographs Computed Excluding Buildings, Trees and Terrain

APPARATUS SYSTEM AND METHOD OF DEPICTING PLUME ARRIVAL TIMES

RELATED APPLICATIONS

The instant patent application is related to U.S. Pat. No. 7,542,884 SYSTEM AND METHOD FOR ZERO LATENCY, HIGH FIDELITY EMERGENCY ASSESSMENT OF AIRBORNE CHEMICAL, BIOLOGICAL AND RADIOLOGICAL THREATS BY OPTIMIZING SENSOR PLACEMENT, issued on June 2009 to Boris et al. (also known as CT-Analyst® (hereafter "CT-ANALYST")), the contents of which is herein incorporated by reference in its entirety.

FIELD OF THE INVENTION

In general, the present invention relates to dangers associated with airborne contaminants released in industrial accidents, spills, and fires or from the deliberate use of Chemical, Biological, or Radiological agents. More particularly, the present invention is concerned with a planning system and method of modeling contaminant transport during an environmental threat or a Chemical, Biological, or Radiological (CBR) threat or obscurant threat and for facilitating effective first responder responses after such threats.

BACKGROUND OF THE INVENTION

Airborne contaminants dispersed in cities, released from industrial accidents, spills, and fires or from the deliberate use of Chemical, Biological, or Radiological (CBR) agents, motivate this work. If there is a significant release of a hazardous contaminant in a heavily populated area, the ability to efficiently provide situational awareness of an incident allows the emergency responder more time to be spent mitigating the problem then trying to understand the output of a less efficient display. The Plume Arrival Time Display that has been developed for CT-ANALYST allows a user to not only efficiently view the incident, but to calculate a faster, more accurate answer than competing solutions. This translates into a faster time to react to a situation, less casualties and the efficient deployment of limited resources. A crisis manager or first responder will usually need to make immediate life and death decisions about how to respond to the airborne threat based on incomplete knowledge of the contaminant source. Even without their dire time constraints, determining wind-driven airflow over a city, accompanied by contaminant transport and dispersion, presents challenging modeling requirements (Boris, J., 2002. The Threat of Chemical and Biological Terrorism: Preparing a Response. *Comp. Science and Engineering* Vol. 4, 2002, pp. 22-32; Britter, R. E. and S. R. Hanna, 2003. Flow and Dispersion in Urban Areas. *Ann. Rev. Fluid Mech.* Vol. 35, 2003, pp. 469-496; Patnaik, G. and J. Boris, 2010. FAST3D-CT: an LES model for urban Aerodynamics Model, Proceedings: *International Symposium on Computational Wind Engineering* 2010, Durham N.C., May 2010). Large, complex-geometry areas and unsteady buoyant flow physics drive computing needs to saturate current modeling capabilities so reasonably accurate runs take from hours to days. Crucial technical issues to be addressed include time-dependent turbulent fluid transport (urban aerodynamics), environmental boundary condition modeling (meteorology), and interaction of the winds with buildings (wind engineering). The advantages of Computational Fluid Dynamics (CFD) using the Large Eddy Simulation (LES) representation include quantifying complex geometry effects, faithfully predicting dynamic nonlinear processes, and reliably treating turbulent dispersion in regimes where experimental model validations are impossible or impractical. The paper, "FAST3D-CT: an LES (Large Eddy Simulation) model for urban aerodynamics" by Patnaik and Boris (2010), considers the performance and validation of such detailed, high-resolution computations and also explains how to make such high quality answers available to crisis managers nearly instantly.

Computational Fluid Dynamics solutions to contaminant transport (CT) can be highly accurate, but are too slow for emergency response and suffer other drawbacks including the need to specify a meaningfully complete initial condition. Therefore, the crisis manager's central dilemma of "fast or accurate" is usually framed by the negative questions: "How slow a run is too slow to be helpful in an emergency?" Or "How inaccurate a prediction might still be acceptable?" However, you can actually have both—speed and the accuracy of a CFD solution. There are applications where computation times of a few minutes or even a few hours might be acceptable but, in a crisis, plume predictions must occur in a few seconds, at most. That is all the crisis managers are really willing to wait. Further, there are also important applications to multi-sensor interpretation and sensor placement optimization that require even shorter computation times.

The U. S. Navy's Naval Research Laboratory in Washington, D.C. has developed Chemical-Biological-Radiological (CBR) crisis management software called CT-ANALYST to solve the critical speed-versus-accuracy dilemma for time-constrained, information-limited users with real operational requirements. CT-ANALYST is both instantaneous (meaning nearly zero computing delay) and accurate. CT-ANALYST is a visual "point-and-click" application and deployable versions of CT-ANALYST are implemented on laptops, workstations and hand-held devices.

Effective defenses of cities, large bases, and military forces against chemical, biological, or radiological (CBR) incidents or attack require new prediction and assessment technology to be successful. The existing plume prediction technology in use throughout the nation is based on Gaussian similarity solutions ("puffs" or "plumes"), including an extended Lagrangian approximation applicable only for large regions and flat terrain where large-scale vortex shedding from buildings, cliffs, or mountains is absent. These current plume methods are also not designed for terrorist situations, where the input data about the source (or sources) is very scant and the spatial scales are so small that problem set-up, analysis and situation assessment must take place in seconds to be maximally effective. Both greater speed and greater accuracy are required.

The CBR defense of a fixed site or region has a number of important features that make it different from the predictive simulation of a contaminant plume from a known set of initial conditions. The biggest difference is that very little may be known about the source, perhaps not even its location. Therefore any analysis methods for real-time response cannot require this information. It is a crucial requirement to be able to use anecdotal information, qualitative data, and any quantitative sensor data available, in order to instantly build a situation assessment suitable for immediate action.

A Discussion of CT-ANALYST: The how and why of Nomografs™ for CTANALYST:

An urban-oriented emergency assessment system, called CT-ANALYST was developed to evaluate airborne Contaminant Transport (CT) threats and aid rapid decisions for regions such as cities where other methods are slow and inaccurate. (Jay Boris, Gopal Patnaik, Keith Obenschein, Laboratory for Computational Physics & Fluid Dynamics, (May 3, 2011) Naval Research Laboratory, Washington D.C. 20375 (2012)).

CT-ANALYST gives both greater accuracy and much greater speed than alternate prediction tools because it embodies entirely new principles to function in the information-starved situations that characterize the first few minutes of a terrorist or accident scenario. CT-ANALYST was designed for the military prior to 9/11 to use verbal and sensor reports, to use mobile sensors, and to function in realistic situations, such as the first few minutes of a harbor spill, where information about the airborne contaminant or Chemical, Biological, Radiological (CBR) agent is highly uncertain. These improvements are made possible by pre-computing very accurate three-dimensional flow solutions that include solar heating, buoyancy, complete building geometry, trees, and impressed wind fluctuations. Detailed 3D simulations for 18 wind directions are pre-computed for coverage regions where CT-ANALYST is to be installed. CT-ANALYST extends these results to all wind directions, speeds, sources, and source locations through a new data structure called Dispersion Nomografs™ (hereinafter "DISPERSION NOMOGRAFS"). We generate these "nomografs" for cities, ports, and industrial complexes well in advance so manager in an emergency need not wait for supporting analyses. CT-ANALYST also provides new real-time functions such as sensor data fusion, "backtracking" reports and observations to an unknown source location, and even evacuation route planning. The resulting capability is faster, more accurate, more flexible, and easier to use than Gaussian and particle-based dispersion models.

I. Introduction

DISPERSION NOMOGRAFS (or just nomografs) are two compact, pre-computed contour maps (data bases) that capture the aerodynamic and turbulent effects of terrain, buildings, vegetation and surface types on the transport and dispersion of contaminant plumes in cities. Standard, well-validated fluid dynamic principles are being used to solve the plume prediction problem in an entirely new way that directly yields the entire "hazard area" at risk of contamination. Most other methods require costly, repetitive computing of many separate contaminant parcels to build up a predicted hazard area. Further, these older methods are only as good as the accuracy of the urban airflow models that they use. With nomografs, improved accuracy and much greater speed are achieved for urban-oriented emergency assessment. By interpolating into these patented nomograf contour maps, we can perform plume predictions and related assessments in milliseconds for wide areas with complex terrain such as cities, ports, and important facilities.

The Naval Research Laboratory ("NRL") high-fidelity 3D, Computational Fluid Dynamics (CFD) model called FAST3D-CT underpins our current implementation of DISPERSION NOMOGRAFS within the CT-ANALYST software system. FAST3D-CT computes multi-gigabyte 3D, contaminant flow-path databases from which the high-resolution DISPERSION NOMOGRAFS are extracted for a city well before CT-ANALYST is ever deployed. Other models that can provide the same fluid dynamic information could, in principle, also be the source of data to build nomografs. For that matter, if enough data could be taken in field trials or experiments, equivalent to three-dimensional fields of the important flow variables over the region, nomografs could then be made from field data.

This short paper describes the principles behind the use and computation of nomografs for predicting the transport and dispersion of airborne contaminants in cities such as Hamburg. It also compares this new approach to older approximate approaches that use Gaussian puffs, Gaussian plumes, or moving particles to predict the plumes associated with contaminant releases. This comparison is offered to show that the same fundamental airflow information is absolutely necessary in all cases, but that this information can be used much more efficiently and accurately in the nomograf representation under the conditions that apply in the first hour or so of a contaminant release within a city.

II. Common Aspects of Using Transport and Dispersion Models

In an accident or other emergency, the starting conditions for most airborne Contaminant Transport (CT) scenario are very poorly defined. The agent, its amount, the source location, the method of release and the release time may not be known. Nevertheless, a rapid, informed response can be crucial because roughly three-fourths of the casualties will be caused in the first 15 minutes in case of a major rupture or other rapid release. Current CT models take a few minutes to set up and run and thus are too slow to support most crises directly. They are also unnecessarily inaccurate because the building geometry and other local details are largely ignored to reduce the necessary computation. Even if one accurate plume can be computed in 5 minutes, we will need 30 minutes to process reports and sensor readings to find ("backtrack" to) an unknown source location and then to predict the plume's path and consequences. In this time most casualties will have occurred. Furthermore, other, better data will have come in that we can't use without starting over.

In some applications, finding the unknown location of a source from sensor readings and reports may be a crucial issue. In others, such as with ships or rail cars, moving and even multiple sources may be involved. When a source location and release time are uncertain and the winds are shifting, such as with expected biological sources, or when a number of sensors have to be placed optimally, many thousands of plume evaluations are needed. These considerations all suggest strongly that faster methods than Gaussian puff, Gaussian plume, or Lagrangian particle models are needed.

Model accuracy is just as important as speed. All methods for computing contaminant transport must know the average air (wind) velocity at each place where the contaminant goes and must have a useable model of the wind fluctuations (i.e. the turbulence and local gusts) in that region. The building geometry determines the velocities and fluctuations in cities and the detailed terrain geometry, including trees will be just as crucial away from cities. Accurate plume predictions can come only from accurate winds, which require accurate geometry. In the interests of speed, other plume prediction schemes generally use large area winds from external sources, such as weather predictions, or else simple formulae to approximate the airflow with random-walk approximations to mock-up the dispersion. Computing the detailed urban Computational Fluid Dynamics (CFD) while you wait is simply far too slow—even when you do know the source and wind initial conditions.

CT-ANALYST distinguishes itself from other models by using accurate pre-computed wind fields to completely circumvent this speed-vs-accuracy dilemma. In principle, this advantage could also give more accurate predictions cheaply in other plume prediction methods but the accuracy of the wind fields they use is not their only performance drawback. The way they use the wind and turbulence fields is also very inefficient. FIG. 7A and FIG. 7B show two diagrams contrasting how the velocity and fluctuation information is used in Gaussian and particle models (left) and how the same information is used for DISPERSION NOMOGRAFS (CT-ANA- LYST-right). The small rectangle represents a building interacting with the flow and increasing dispersion.

III. Using Wind Velocities for Gaussian Puff and Nomograf Models

In Gaussian puff models, each puff moves with the wind and has a finite size that grows from the local turbulence. Each puff center is moved during a time step using an average wind velocity at the puff center. In the vertical this average wind velocity is usually computed using knowledge of the atmospheric velocity profile near the ground but the typical horizontal resolution of these winds is one or two kilometers. This is at best a number of city blocks, making accurate treatment of the dispersion caused by urban geometry impossible.

Gaussian puff methods on the left in FIG. 7A use the wind velocity at the puff center to determine where the center moves and use the fluctuations, represented by the arc(s), to determine how much the puff spreads during a timestep. Using nomografs, the left edge of a contaminant plume moves in the direction of the leftward turbulent deflections of the average velocity and the right edge moves in the direction of the rightward deflections. In FIG. 7B, the zig-zag line shows how the left plume edge is deflected around a building.

The Gaussian puffs each have a different, constantly changing, exponentially decreasing "Gaussian" density profile that they carry around with them. Each profile approaches zero in the outer regions of the puff, as indicated by the shading of the orange ellipse in the figure above. This puff profile is the exact solution of a diffusion equation for the puff material (gas or particles) when the wind velocity and turbulence are constant everywhere, but this is only a crude approximation at best. When the puff is small, its motion and spreading results from distortions, vortices, and local shear flows and these are not well represented as diffusion. When the puff is large, diffusion becomes a more correct physical model but the turbulence and velocity are quite variable across the puff. The overall contaminant density at any time is computed as the sum of all these individual density profiles at each point.

By way of contrast, the panel on the right in FIG. 7B shows how the local average velocity and turbulent fluctuations (arc) are used in CT-ANALYST via nomografs. Two composite directions are computed for the contaminant plume, the limiting direction that the right edge would take, and the limiting direction that the left will take. These directions will be the same when the velocity is completely steady; the contaminant then moves with the wind but does not spread. However, when the actual velocity at each point is fluctuating due to turbulence, there is a maximum displacement of the contaminant to the right of the average velocity and there is a maximum displacement to the left. In this approach, the entire plume is defined between the limiting right and left edges, and these edges can be computed as simple one-dimensional integrals. Since the velocity fields, pre-computed using the FAST3D-CT code, are typically resolved to 5 or 6 meters, the geometric accuracy of these edge calculations is far higher than can be approximated by Gaussian puff, particle, or plume approximations.

FIG. 8 schematically indicates the beginning of the detailed solution procedure for Gaussian puff models. Many puffs, a few each time step, are generated in the source region and are moved away downwind. A number of time steps are used to track each puff as it moves and expands. These timesteps are extrapolations mathematically and so become less accurate the longer the steps are. To improve accuracy, puffs are split up when they become too large, a process that slows computation. To save unnecessary computer cycles, puffs are also merged when there are a number of them overlapping. This necessarily reduces accuracy and increases program complexity.

As illustrated in FIG. 8, a sequence of Gaussian puffs original at the source circle on the left and move along the average wind direction indicated by the curved black line. These puffs spread according to the strength of the velocity fluctuations along the puff centerline. This spreading is indicated by the change in size, as each succeeding puff gets larger.

The important prediction in most crises is the expected hazard area to avoid. FIG. 9 shows schematically how this Gaussian puff information is used to compute a hazard area, indicated by the red line, for the overall plume. This line is generally defined where the summed density of the outermost puffs drops away below some predetermined threshold or where some health consequence is minimal. Each puff has its own density profile that can be expensive to compute; each of these profiles is fuzzy; and these profiles all overlap everywhere. Therefore, to find the hazard area for the plume, conventional models must add the profiles together at each point to get the composite density before identifying, within the fuzzy plume boundary, what defines a particular hazard area.

Referring to FIG. 9, the hazard area for the plume is shown as the circumferential line drawn around the summed density profile of all the puffs at a specified threshold value. This value depends on a definition of the hazard or health consequences that may require appreciable extra computation.

When different sources of contaminants interact, it is necessary to repeat the above procedure for each source and the overall procedure is very slow, generally taking minutes to compute even on today's computers. The procedure is also relatively inaccurate because the underlying mathematical assumptions are questionable in the urban context and because the wind fields are neither accurate nor well resolved.

IV. Fluid Dynamic Principles Used in DISPERSION NOMOGRAFS

FIG. 7A and FIG. 7B above showed schematically how the local average velocity and turbulent fluctuations could determine paths through the urban landscape defining the left and right plume edges rather than computing the center motion and spreading of a large number of puffs. This alone is a major computational saving because the edges can be integrated more accurately at less cost when the hazard areas are computed directly. There is an additional major saving that this alternate approach makes possible. All plume edge paths, since they depend on the underlying wind and turbulence fields that have been pre-computed, can also be pre-computed, tabulated, and stored for instant look-up. Nomografs record these limiting left and right plume edge paths in a very compact data structure that serves for all source locations within the urban "canopy," (i.e. near the ground).

The following is a discussion of the approximations which make this plume edge approach, as implemented in nomografs, efficient and effective. Please remember that the accuracy of the winds fields used determines the accuracy of the contaminant plume regardless of the computer algorithms used. This was discussed above with regard to the importance of accurate terrain and accurate building geometry. The fluid-dynamic principles that are central to the current DISPERSION NOMOGRAFS representation and its subsequent applications are stated in P1. through P4. as follows:

P1. A contaminant transports dynamically via convection with the local air velocity; this is not diffusion. All relevant transport and dispersion arises from resolved (and possibly unresolved) fluid motions. Diffusion, per se, plays only a minimal role.

P2. Vertical spreading of contaminant is quick on the building scale in an urban environment. Both simulations and field trials support this observation, allowing a two-dimensional computation of the hazard "area" as a footprint for a fully three-dimensional plume representation.

P3. Maximum lateral dispersion of contaminants occurs near the ground because the buildings cause strong transverse turbulence down where the average wind speed is relatively slow. As a result, the direction of the asymptotic plume edges is determined entirely locally with no need to know where the source is. The further spreading of any small parcel of contaminant that arrives at a location only depends on what happens there.

P4. Wherever the contaminant goes becomes contaminated and a volume, once contaminated, stays contaminated. This is a conservative approximation favored by first responders to aid in "safe siding" the predictions. It could (perhaps) be relaxed considerably for applications in open regions or over water.

Because fluid dynamic turbulence is not diffusion (Principle P1), plume edges are actually quite sharp, not fuzzy as assumed with puffs, but the actual location of this sharp edge can be rather uncertain. We may not be able to predict exactly where the edge of the plume is at any instant and we call this variability—but the edge at any instant will be quite sharp. FIG. 10A, FIG. 10B, FIG. 10C, FIG. 10D, FIG. 10E, FIG. 10F, FIG. 10G, FIG. 10H and FIG. 10L below show eight different plumes computed 20 minutes after an $SF_6$ trial release over downtown Los Angeles using the same input winds and weather. Each of these instantaneous plume snapshots has a quite sharp edge although the overall plume shapes are noticeably different.

Eight different plumes result because the local wind fluctuations were all somewhat different because the contaminant clouds were released at eight different times. These are called different "realizations" and a very important conclusion is that there is no one single "unique" answer. No one of these realizations is more accurate or more "correct" than any other.

As indicated above, FIG. 10A, FIG. 10B, FIG. 10C, FIG. 10D, FIG. 10E, FIG. 10F, FIG. 10G, FIG. 10H and FIG. 10L illustrate eight different realizations computed for a single source. These are compared with Tracer ES&T sampler data from downtown Los Angeles (squares). The wind is from 170° at 3 m/s with moderate fluctuations. The point releases are 5 min in duration with measurements (2.5 min sampling intervals) at each of 50 locations within about 1 km source at the lower circle/dot at the bottom of FIG. 10L. Estimating variability requires multiple trials. There is no correct or "unique" answer!

Another important fluid dynamic consideration in using plume edges paths (nomografs) to determine a hazard area is to decide that a point stays contaminated once it has been contaminated (Principle P4.). In light of the essentially unpredictable variations shown in FIG. 10A through FIG. 10H and FIG. 10L, the safest approach is to take the worst of the realizations as defining the "envelope," the outer boundary, of the hazard area. FIG. 11A, FIG. 11B, FIG. 11C and FIG. 11D show plume envelope construction schematically at a particular time after the contaminant release begins, shown as four different light shaded plumes, labeled (a) to (d). Each is a possible realization of the plume from the source at the red circle. The dark shaded circumferential "envelope" drawn in behind each of these realizations is the ideal hazard area we would like to predict if these four realizations were the only possible solutions. Each plume fills out a different fraction (percentage) of the composite hazard area and there is a probability that each point in the hazard will be contaminated by any particular realization.

Thus, FIG. 11A. FIG. 11B. FIG. 11C and FIG. 11D illustrate four different plume realizations (light shaded areas) of a single source are overlaid on the plume envelope, here defined as the union of all these plume realizations. Since there is no one "correct" answer, the plume envelope gives a hazard area that evolves in time and generally provides a safe, conservative estimate of the area that could be contaminated.

The concept of a two-dimensional plume envelope is useful because the maximal lateral spreading of the plume is determined near the ground (Principle P2.) and this lateral extent is not very different up to the average height of the buildings (Principle P3.). This construct "safe sides" the predicted hazard area because it is not based on an average of the realizations, as with most Gaussian averaging models, but rather is the union of worst cases. The probability that any particular location outside the plume envelope will be contaminated at time t will be small and can be made smaller by making the plume envelope a little bit larger.

V. Computing Limiting Plume Envelope Edges: DISPERSION NOMOGRAFS

This new approach, to find the limiting plume envelope edges directly, is both safer and faster. The main limitation is that the prediction will be confined to the domain where the CFD computations for the nomografs have been performed and to sources within the urban canopy (i.e. near the ground). Nomografs for areas as large as 40 km by 30 km have been computed and methods exists to extend the nomograf approach to long-time variations in the winds but the predictions are generally limited to an hour or two, unless the winds are quite steady, and to the first 10- to 20 kilometers downwind of the source.

When an agent density (concentration) is desired, a simple polynomial profile is interpolated into the three-dimensional extension of the plume envelope above the surface. Our algorithms use the DISPERSION NOMOGRAFS tables to determine the spatial distribution of the agent density within the plume envelope. In this way only one simple polynomial evaluation is computed at each point inside the plume envelope and none are performed outside the envelope. Meanwhile, the nomografs transfer information about the local geometry into the approximate density profiles. This approach implicitly depends on principles P2. and P3. stated above.

To summarize this new approach schematically, look at FIG. 12 below. The limiting left plume edge is computed by integrating along a direction given by taking the average wind direction near the ground and deflecting this direction to the left by the strength of the fluctuations. On the upper blue curve, labeled "left edge" in the figure, a black arrow in the local average wind direction is shown. The blue wedge at this location indicates the left and right fluctuations of the wind velocity that go into building up this average wind direction. It is clear that a different right edge can be started at each point along the left edge. The limiting right plume edge that originates at the right (lower) edge of the source is determined just as the left edge is and diverges to the right of the left edge by an amount that depends on the local fluctuations divided by the average wind speed. It is also clear that a new left edge could be started at each point along the chosen right edge.

FIG. 12 illustrates the result of computing left and right plume edges to bind the transport and dispersion of a contaminant. Individual components (puffs) in the Gaussian puff method are shown in grey to indicate the relationship between the different approaches.

FIG. 12 also shows a red line used to cap off the plume envelope at any particular time. The distance of this end cap from the source depends on the time that has elapsed after the release has begun and the distribution of wind speeds over the domain. It should be obvious that these edge integrals could be performed for each source scenario separately and the resulting hazard area prediction would be a lot faster than current methods and more accurate, as long as detailed, pre-computed wind and turbulence fields are used.

As mentioned above, however, P1. and P3. taken together, mean that the limiting left and right edge directions for a small parcel of contaminant near the ground, at any place in the domain, cannot depend on where that parcel came from. As a result, the limiting left and right edges extend all the way across the domain and only need to be computed once and stored. This is what DISPERSION NOMOGRAPS are designed to do (FIG. 13 below). The nomografs are contour maps of the domain, one for the right edges and one for the left, where the edges originating at a location $(x^s, y^s)$ are defined by the contour levels $R(x,y)=R(x^s,y^s)$ and $L(x,y)=L(x^s,y^s)$.

This definition is "Gauge invariant" mathematically, meaning that the particular "height" values used to label the contours are irrelevant, only the geometry of the limiting plume edge curves through the domain matters. In this approach, given a source location, we can look up the plume edges directly from the nomografs so the procedure is very fast! The nomografs can encode very accurate edge shapes and each left and right edge contour can be used for many sources. Therefore the representation is very compact as well as very fast to apply. Calculation times for hazard areas take only a few tens of milliseconds with accurate edge shapes and computing a density profile inside the plume envelope takes only two or three times longer.

FIG. 13 below indicates schematically how the same left and right edge contours can be used, even simultaneously, for multiple sources. For simplicity a single limiting left edge contour (thicker blue line) and a limiting right edge contour (thicker black line) have been duplicated above and below to show what an idealized nomograf would look like. A situation exactly like this would occur if the average wind direction and the corresponding turbulence fluctuation strength were to depend only on the horizontal coordinate (x) but not the vertical coordinate (y).

FIG. 13. Left edges (i.e., plume edge paths depicted by lines illustrated at the top half of FIG. 13) and right edges (i.e., plume edge paths depicted by lines illustrated at the bottom half of FIG. 13) limiting plume edge paths can be nested into a data structure containing two contour maps as shown. Because the contaminant plume edge directions are determined near the ground, this direction is the same whether near the source, in the middle of the plume, or near the downwind boundary. Three plume envelopes are shown.

Even though the wind fields leading to FIG. 13 are constrained and artificial, we can still see that plumes originating in different places have different shapes. The dark shaded circles indicate three source locations. The source on the left side of FIG. 13 shares its right edge with the lower source and shares its left edge with the upper source so the resulting larger shaded plume envelope would eventually spread to cover the other two plumes in the upper middle and on the right. In this figure, the source on the left has been active for twice as long as the upper source and about three times as long as the lower (rightmost) source.

VI. Computing DISPERSION NOMOGRAFS from FAST3D-CT Runs

The data collected for nomograf generation in a FAST3D-CT urban aerodynamics simulation include:

D1. The three-dimensional means and standard deviations of the three velocity components of the airflow computed from data collected at seven ground-conforming height levels from the ground to above the height of the typical buildings. This collection covers an interval of at least 30 minutes and often an hour after a run initiation "spin-up" period.

D1a. Average over the collection interval of the X- Y- and Z-components of the air velocity at the seven chosen heights.

Dab. Standard deviations of the wind velocity components around the average values at the seven heights measuring both resolved fluctuations and turbulence.

D2. Six key quantities are accumulated at two different heights for each of a number of sources that are initialized after the CFD model "spin-up" period is complete and the statistics of the fluctuation urban aerodynamics have stabilized.

D2a. First arrival time (sec) of contaminant density exceeding a threshold value at each location, D2b. Time of arrival (sec) of the maximum contaminant value at the location, D2c. Decay time (sec) after the maximum is reached at the location, D2d. Local peak contaminant density ($gm/m^3$) at any time, D2e. Integrated contaminant density at the location (dose=sec $gm/m^3$), D2f. Local contaminant variability, measured as the integrated total variation ($gm/m^3$).

A typical run with the FAST3D-CT model for a complex urban area of 30 square km resolved with 6 m cells takes 12 hours on a 16-processor Silicon Graphics Inc. ("SGI") computer system. This is significantly faster per square km than classical CFD models due to the savings achieved by our MILES turbulence model, our efficient treatment of the complex geometry, and other algorithmic improvements including efficient parallel processing. Because of the FAST3D-CT model efficiency, we can compute a set of DISPEERSION NOMOGRAFS for each eighteen different wind directions in a few days of computing on what is really a rather modest "supercomputer."

The right and left DISPEERSION NOMOGRAFS edge contours are computed geometrically by integrating along the right and left edge directions as constructed in FIG. 7B, i.e., in the panel on the right. The actual computational procedure is very similar to computing a stream function for a potential flow problem by integrating along the steady streamlines. Right edges cannot cross or join each other in nomografs. Similarly the left edges cannot cross or join each other. The actual direction for the edge contour at a point is computed as a weighted average of the local wind velocity components (D1a) plus (right) and minus (left) the standard deviations (D1b) over the seven height levels recorded in D1 above. The heaviest weighting is at or below the height of the typical buildings, as required by principles P2. and P3. above.

While the nomografs themselves depend only on the geometric velocity data, the data items in D2 are used to calibrate the scale factor that multiply the standard deviations (arcs) in FIG. 7A and FIG. 7B. Thus this scale factor controls the overall left and right deflections of the plume edges from the average wind direction; the calibration with the FAST3D-CT items in D2 ensures the overall dispersion encoded in the nomografs agrees with the CFD simulations. These D2 data are also used to calibrate the formulae and interpolations used by CT-ANALYST to convert the nomograf edge contours to on-screen predictions. Not coincidentally, the quantities indicated in D2 are virtually the same definitions and are computed exactly as for the short-duration releases in the Hamburg wind tunnel in the recent FAST3D-CT validation projects using Oklahoma City trials and matching wind tunnel studies. Thus there is a rather direct trail from the experiments and the data taken there directly through the detailed CFD simulations to the CT-Analyst predictions.

Speaking on a more operational level, the four steps in generating and using DISPEERSION NOMOGRAFS for a city are:

1. An accurate geometry database is compiled from Light Detection & Ranging ("LIDAR"), stereo imagery, or shape files. The geometry database used by FAST3D-CT is a two-dimensional (typically one meter resolution) array that returns the heights of terrain, buildings, and trees, and surface composition in the computational domain. Other, more complex forms can be used and reduced to the required FAST3D-CT input.

2. Detailed 3D computational fluid dynamics calculations (FAST3D-CT) are repeated for 18 wind directions spaced 20 degrees around the compass and the results for each run are captured in an extensive database. These simulations include the appropriate urban boundary layer for the region with realistic turbulent fluctuations imposed at the inflow boundaries. Multiple releases are tracked in each case as described above.

3. The salient features from the CFD database are distilled into DISPEERSION NOMOGRAF plume edge contour maps for rapid interactive access. The nomografs primarily capture how the local building geometry affects the shape of the plume envelopes. Time integration is thus replaced by interpolations that capture the aerodynamic effects of the full urban geometry.

4. The nomograf tables then are encrypted and input to the CT-ANALYST software, an easy-to-use graphical user interface (GUI) for instantaneous situational analysis. Plume computation, for example, takes less than 50 milliseconds. An actual example is shown in the next section below.

FIG. 14A and FIG. 14B below show an example of the left and right edge nomograf tables for a small island domain with the wind from the north (top). The grayscale shading coding of the left edge nomograf (FIG. 14A) and the right edge nomograf (FIG. 14B) shows that these two arrays are indeed contour maps with darker shading in FIG. 14A indicating low (negative) values and lighter shading indicating larger (positive) values (see FIG. 14B). The broad lines, alternating light and dark shading in FIG. 14A and FIG. 14B, identify a few of the limiting plume envelope edge contours. The width of these lines indicates qualitatively the spreading which a parcel of contaminant would undergo at that location. This visualization helps show the relationship of large lateral dispersion of the plume edges, and therefore also in the contaminant plumes, to the underlying geometry. The higher and denser the buildings, the more the plume edges are deflected from the mean wind direction. This figure also shows that the plume edge contours are essentially straight over flat open areas such as the water.

FIG. 14A and FIG. 14B illustrate left edge (left panel) and right edge (right panel) respectively, DISPEERSION NOMOGRAF contours for a fictitious island kingdom called Atlantis. The wind is from the top and the alternating purple and grey bands illustrate several of the nomograf plume envelope edge contours.

VII. Using DISPEERSION NOMOGRAFS: CT-ANALYST Examples

FIG. 15 uses CT-ANALYST to compute plume envelopes for two sources located at the blue stars below. These were computed using the DISPEERSION NOMOGRAF shown in FIG. 14A and FIG. 14B. The crosshatched bands can be seen to be the same as in FIG. 14A and FIG. 148 overlaid on the CT-ANALYST screenshot. FIG. 15 illustrates the relationship of plume envelopes and contamination footprints to the underlying DISPEERSION NOMOGRAF.

FIG. 15 illustrates two distinct plume envelopes from CT-ANALYST which are shown in relationship to the underlying nomograf edge contours. The plume footprints, shown in solid grey behind the plume envelopes, are defined (downwind) exactly as filling the region between the left and right plume edge contours.

FIG. 16 below shows the entire CT-ANALYST interactive control screen for an urban area, in this case a section of downtown Washington D.C. prepared to support the 2005 and 2009 inaugurations. The contaminant concentration display (varying shades of shaded contours) for the source at the star (at the bottom of the FIG. 16) is overlaid on the contamination footprint (shaded gray region). Star-shaped nodes are sources, triangular and circular nodes are sensor reports, and square nodes indicate specific sites. When a source node is active it is illustrated with light shading. Footprints, plume envelopes, contaminant concentration plots, and escape routes can be displayed for sources by activating buttons on the lower portion of the CT-ANALYST screen. Triangular sensor report nodes inside an active plume envelope are "hot" (SOLID SHADING) while those still uncontaminated are "cold" (light shaded triangle within the shaded triangle). In this example all the site displays are inactive as shown by the buttons. Downwind consequence regions (for active "hot" reports) and upwind backtrack estimates (for all active "hot" and "cold" reports) can be displayed for individual sensor nodes, indicated by filled triangles. Contamination zones from downwind leakage and upwind danger zones can be plotted for all square site nodes (light shaded when they are active). The diagonal shaded lines are the recommended evacuation (escape) routes.

FIG. 16 is a CT-ANALYST full screen shot showing contaminant density contours the contamination footprint, and evacuation routes overlaid on a Washington D.C. city map. The wind is from the southeast. Evacuation routes are optimized to minimize inhaled contaminant doses. The dark region in the lower middle of the display is the result of the CT-ANALYST backtrack operation. Several "hot" sensors and two "cold" sensors were used to "backtrack" to a source location estimated using a union of the upwind "danger zone" capability.

To compute displays such as danger zones, plume envelopes, and backtracks to unknown source locations, knowing the actual concentration of the airborne agent is not necessary. Indeed, until the total amount of the contaminant is known, plotting the actual concentration distribution isn't even possible. Therefore, CT-ANALYST provides a relative concentration until the mass of the agent from a specific source can be estimated. Fortunately, this relative concentration and its time history are all that is needed to select civil defense options that minimize the inhaled dose of contaminant. The normalization used for FIG. 10 was chosen to correspond to the integrated mass of the source used in the corresponding FAST3D-CT simulations used to develop the nomografs. This normalization also accounts for the contaminant that leaves the grid through an analytic extension of the nomograf data arrays.

The two panels in FIG. 17A and FIG. 17B below were taken from cropped CT-ANALYST screen shots for a region in downtown Washington D.C. using two different nomograf tables. Panel (a) (FIG. 17A) shows three different nomograf-based displays computed 6 minutes after a release has occurred at the source indicated by the light blue star using nomografs that encode the actual detailed Washington D.C. geometry resolved to 1-meter accuracy. The source of contamination may be an accident, a leaking sprayer, or a broken container of hazardous chemicals that needs to be analyzed. Panel (b) (FIG. 17B) shows the corresponding predictions when the detailed geometry is ignored. The closed pink contour in each panel shows the 6-minute plume envelope when the wind is 3 meters per second from the west-northwest. The plume envelopes show the geographical region that the contaminant plume could have reached during its expansion up to the indicated time after release. The corresponding contamination footprints (grey) behind the plume envelope in FIGS. 11a and 11b respectively, represent the full extent of the growing contamination region after the plume envelope has spread to its maximum toxic extent. The actual contaminant plume envelope starts at the source near the upwind corner of the footprint and expands downwind away from the source as time increases.

FIG. 17A and FIG. 17B illustrate DISPEERSION NOMOGRAFS in CT-ANALYST capture building aerodynamics. a) Nomograf results with full building geometry. b) Nomograf computed excluding buildings, trees, and terrain. The figure shows the corresponding contamination footprints (darker gray), plume envelopes after 6 minutes (lighter gray), and the upwind danger zone of a site (grayscale in the upper left corners of FIG. 17A and FIG. 17B).

The plume envelope and contamination footprint in Panel (b) see (FIG. 17B) are computed in exactly the same way as in Panel (a) (see FIG. 17A) except that the geometry used for the nomografs is flat and featureless. As a result the plume envelope is symmetric, exactly wind aligned, and shows none of the local dispersion caused by the actual building complexes whose effects are illustrated in Panel (a). Such a simple, non-physical result would be expected from Gaussian puff models using average roughness coefficients and even from Gaussian plume models. The results, however, are wrong. Even a quick look at such results displayed generally makes most people suspicious.

The shaded regions in FIG. 17A and FIG. 17B show estimations of the upwind danger zone for the chosen site (bright square) with and without capturing the effects of the geometry, respectively. The danger zone for a site is the set of all possible positions upwind where a source of contamination could reach the site. Computing the danger zone is an entirely new capability made possible by the nomograf representation and algorithms. Notice the difference caused by the local variations of the city geometry. In (b) (i.e., FIG. 17B), without proper representation of the geometry, the source (shaded star) is outside the predicted danger zone (dark shaded) and the plume envelope (lighter shaded) areas and therefore does not reach the site. In (a) (i.e., FIG. 17A) however, the extra northward dispersion from the buildings causes the plume envelope to reach the green square (site). In turn, CT-ANALYST shows, via the danger zone, that the given site can be threatened from the location of the star. Clearly the predictions using the correct geometry are "safer."

Sensors are indicated in these figures with triangular icons. Shaded sensor icons have not been triggered by contaminant at the time depicted in FIG. 17A and FIG. 17B, as they lie outside of the instantaneous plume envelope. Some sensors and sites will lie outside the footprint with flat-earth geometry but inside the footprint when full geometry is used. In other words, a prediction that does not account for complex geometry gives a false negative result for many locations, possibly resulting in unnecessarily high losses. An emergency response tool that does not account for complex geometry will be unreliable at best. Some conventional plume software greatly overestimates the size of a plume envelope, particularly near the source, to avoid these geometry-induced false negatives. Severe overestimates can also have dangerous consequences. People may be inclined to stay in a dangerous location, thinking an uncontaminated region is too far away to reach.

VIII. Summary:

All methods to compute the transport and dispersion of airborne contaminants need to use a representation of the wind field over the region of interest. Only when this representation of the wind field is accurate can the plume prediction be reliable. Providing an accurate, building-scale approximation of the wind field is a slow, costly computational process, far too slow for emergency applications while the responsible officials (users) wait. Therefore conventional CT models generally use unresolved constant parameter winds (for Gaussian plume models), very poorly-resolved wind field estimates that they can get quickly from other sources (for Gaussian puff models), or possibly phenomenological wind/building interaction models (for Lagrangian particle models). These models still do a lot of computing while the users wait, eventually arriving at hazard-area predictions after several minutes that have obvious inaccuracies and other limitations.

In these earlier rather inaccurate, city-scale predictions, the specification of atmospheric stability classes and many other global properties about the agents and source dispersion mechanisms fosters a kind of intellectual misrepresentation that misleads users, projecting a false sense of reliability for the models. For example, specifying the temperature and pressure of a toxic agent like chlorine and then asking a user to state the size hole that the chlorine is coming out of gives the impression that the heavier-than-air aspects of the release are being properly accounted for. Actually the type of surface, such as sand, water, or concrete, its heat transfer properties, and the slope of the terrain are even more important and yet totally neglected.

By way of contrast, this discussion shows that the hazard area of a CT scenario can be computed quickly, accurately, and directly using detailed, pre-computed wind fields that properly capture individual building effects. This approach leads to a very efficient representation in terms of DISPERSION NOMOGRAFS where the plume envelope edges are recalled from compact, contour-map databases. In our implementation a state-of-the-art CFD model, FAST3D-CT, pre-computes the complete time-dependent 3D urban aerodynamics with full urban geometry at high resolution (2-6 meters). In this way there is no operator delay in using the very best wind velocity fields available. DISPERSION NOMOGRAFS recall the results of these high-resolution 3D simulations with no time delay for transport and dispersion (T&D) calculations of many puffs/particles over many time steps.

The instant response CT-ANALYST format using nomografs also allows quick sensor fusion operations and permits users to "backtrack" to unknown source locations with actionable information in a few milliseconds. DISPERSION NOMOGRAFS are faster because they provide plume edges directly rather than computing them laboriously while the user waits. This approach is more accurate primarily because there is no user delay in using the very best wind velocity fields that can be had. CT-ANALYST is also more robust because there is essentially no computation to go bad, very little input is needed, and the displays are intuitive. The software that is easier to use because it is simpler.

Contemporary common-use hazard prediction and consequence assessment systems:

Contemporary common-use hazard prediction and consequence assessment systems have at their heart a plume simulation model based on a Gaussian plume/puff model. These systems typically employ Gaussian plume simulation models. The Gaussian plume method, while relatively fast, tends to be inaccurate, especially for urban areas. The setup for all these systems tends to be complicated, and require prior knowledge of the source characteristics.

Some examples of common-use hazard prediction and assessment systems are as follows:

CATS (Consequences Assessment Tool Set) is a consequence management tool package, developed by the U.S. Defense Threat Reduction Agency, U.S. Federal Emergency management Agency, and Science Applications International Corp, that integrates hazard prediction, consequence assessment, emergency management tools, including the Hazard Prediction and Assessment Capability (HPAC) system, and critical population and infrastructure data within a commercial Geographical Information System. (CATS: Consequences Assessment Tool Set, U.S. Defense Threat Reduction Agency, U.S. Federal Emergency management Agency, and Science Applications International Corp.; SWIATEK et al. "Crisis Prediction Disaster Management", SAIC Science and Technology Trends II, Jun. 24, 1999).

CAMEO® (Computer Aided Management of Emergency Operations) is a system of software applications used to plan for and respond to chemical emergencies. It is one of the tools developed by EPA's Chemical Emergency Preparedness and Prevention Office (CEPPO) and the National Oceanic and Atmospheric Administration Office of Response and Restoration (NOAA), to assist front-line chemical emergency planners and responders. (CAMEO: Computer Aided Management of Emergency Operations, EPA's Chemical Emergency Preparedness and Prevention Office (CEPPO) and NOAA; CAMEO "Computer Aided Management of Emergency Operations," U.S. Environmental Protection Agency, May 2002, pp. 1-306).

MIDAS-AT™ (Meteorological Information and Dispersion Assessment System —Anti-Terrorism), a product of ABS Consulting Inc. is a software technology that models dispersion of releases of industrial chemicals, chemical and biological agents, and radiological isotopes caused by accidents or intentional acts. MIDAS-AT is designed for use during emergencies and for planning emergency response drills. Its Graphical User Interface (GUI) is designed for simple entry of information required to define a terrorist scenario (MIDAS-AT Meteorological Information and Dispersion Assessment System—Anti-Terrorism: ABS Consulting).

HPAC (Hazard Prediction and Assessment Capability), developed by the Defense Threat Reduction Agency, is a forward-deployable, counter proliferation-counterforce collateral assessment tool. It provides a means to predict the effects of hazardous material releases into the atmosphere and its impact on civilian and military populations. The HPAC system also predicts approximate downwind hazard areas resulting from a nuclear weapon strike or reactor accident and has the capability to model nuclear, chemical and biological weapon strikes or accidental releases. (HPAC: Hazard Prediction and Assessment Capability, DTRA, HPAC Version 2.0 and HASCAL/SCIPUFF Users Guide, Defense Special Weapons Agency, July 1996; "Hazard Prediction and Assessment Capability" Fact Sheet, Defense Threat Reduction Agency Public Affairs, pp. 1-2).

VLSTRACK (Vapor, Liquid, and Solid Tracking), developed by Naval Surface Warfare Center, provides approximate downwind hazard predictions for a wide range of chemical and biological agents and munitions of military interest. The program features smart input windows that check input parameter combinations to ensure that a reasonable attack is being defined, and simple and informative output graphics that display the hazard footprint for agent deposition, dosage, or concentration. The model also features variable meteorology, allowing for interfacing the attack with a meteorological forecast. (VLSTRACK: Vapor, Liquid, and Solid Tracking, [U.S. Pat. No. 5,648,914] Naval Surface Warfare Center, Bauer, T. J. and R. L. Gibbs, 1998, NSWCDD/TR-98/62, "Software User's Manual for the Chemical/Biological Agent Vapor, Liquid, and Solid Tracking (VLSTRACK) Computer Model, Version 3.0," Dahlgren, Va.: Systems Research and Technology Department, Naval Surface Warfare Center).

ALOHA (Areal Locations of Hazardous Atmospheres), from EPA/NOAA and a component of CAMEO, is an atmospheric dispersion model used for evaluating releases of hazardous chemical vapors. ALOHA allows the user to estimate the downwind dispersion of a chemical cloud based on the toxicological/physical characteristics of the released chemical, atmospheric conditions, and specific circumstances of the release. Graphical outputs include a "cloud footprint" that can be plotted on maps to display the location of other facilities storing hazardous materials and vulnerable locations, such as hospitals and schools. (ALOHA®—Arial Locations of Hazardous Atmospheres, EPA/NOAA; "ALOHA Users Manual", Computer Aided Management of Emergency Operations, August 1999, pp. 1-187).

FASTD-CT (FAST3D—Contaminant Transport) is a time-accurate, high-resolution, complex geometry CFD model developed by the Laboratory for Computational Physics and Fluid Dynamics at the Naval Research Laboratory. The fluid dynamics computations are performed with a fourth-order accurate implementation of a low-dissipation algorithm that sheds vortices from obstacles as small one cell in size. Particular care has been paid to the turbulence treatments since the turbulence in the urban canyons lofts ground-level contaminant up to where the faster horizontal airflow can transport it downward. FAST3D-CT has a number of physical processes specific to contaminant transport in urban areas such as solar chemical degradation, evaporation of airborne droplets, re-lofting of particles and ground evaporation of liquids. (FAST3D-CT: FAST3D—Contaminant Transport, LCP & FD, NRL Boris, J. "The Threat of Chemical and Biological Terrorism: Preparing a Response," Computing in Science & Engineering, pp. 22-32, March/April 2002).

NARAC (National Atmospheric Release Advisory Center) maintains a sophisticated Emergency Response System at its facility at Lawrence Livermore National Laboratory. The NARAC emergency response central modeling system consists of a coupled suite of meteorological and dispersion models. Users access this system using a wide variety of tools, also supplied by NARAC. Users must initiate a problem through a phone call to their operations staff or interactively via computer. NARAC will then execute sophisticated 3-D models to generate the requested products that depict the size and location of the plume, affected population, health risks, and proposed emergency responses. (NARAC: Atmospheric Release Advisory Capability, Lawrence Livermore National Laboratory, "Forewarning of Coming Hazards," Science & Technology Review, pp. 4-11, June 1999, Lawrence Livermore National Laboratory).

Contemporary tools, such as the FASTD-CT: FAST3D-CT and NARAC, capable of providing engineering-quality 3D predictions are reliable, but they take a long time, i.e., hours and/or days to set up, run and analyze, before results are returned.

All of the above-mentioned systems take several minutes, hours, or even days to return results. Simplified systems such as PEAC® (Palmtop Emergency Action for Chemicals) [U.S. Pat. No. 5,724,255], originally developed by Western Research Institute, provide the necessary emergency response information to make quick and informed decisions to protect response personnel and the public. PEAC-WMD 2002 provides in hand information compiled from a number of references with very fast recall. PEAC provides emergency responders with instant access to information from a number of sources and evacuation distances based on several sets of guidelines. This system, can return results within seconds and requires less detailed knowledge of the source, but the resulting fixed-shape plume does not take into account any effect of complex terrain or buildings.

Waiting even one or two-minutes for each approximate scenario computation can be far too long for timely situation assessment as with contemporary common-use hazard prediction systems. Overly simplified results can result in inaccurate results. The answer to this dilemma is to perform the best computations possible from state-of-the-art 3D simulations well ahead of time and capture their salient results in a way that can be recalled, manipulated, and displayed instantly.

In many emergency response scenarios, in addition to knowing the severity of the effects, it is important to know how much time is available before any deleterious effects will occur. The time required for the plume to reach a given location, the arrival time, will influence the response: ranging from a simple shelter-in-place to outright evacuation. While most of the contemporary models described are capable of calculating the arrival time of a contaminant, they typically present this information inefficiently. For example the predictions of a plume at 5, 15, 30 and 60-minute after release are presented to the user as four separate images, and the arrival time at a specific site cannot be determined.

Therefore, the need exists for a software emergency assessment tool which is easy to use and effective instantaneously providing immediate assessment of new data, instantaneous computations of exposed and soon-to-be exposed regions, and the zero-delay evaluations of options for future actions. The software should also be capable of projecting optimal evacuation paths based on the current evolving situation assessment.

Further, the need exists for a new tool which is much faster than contemporary "common use" models with accuracy comparable to three-dimensional, physics-based flow simulations for scenarios involving complex and urban landscapes. The focus is on situation assessment through sensor fusion of qualitative and incomplete data.

Further, the need exists for a solution to the current inefficient attempts of detailing the severity of contaminant effects, by providing a unified display which efficiently depicts the contaminant severity elements along with additional components which are invaluable when making decisions where lives are at risk.

SUMMARY OF THE INVENTION

Computer implemented methods and systems work cooperatively to calculate and display plume arrival time of a CBR contaminant and to alert responders to take action, associated with mitigating the CBR contaminant. The methods and systems comprise, performing, plume arrival time operational use routines, including: sensing an unknown CBR contaminant released in a geographic area of interest and then, over a communications network, alerting and causing responders to mitigate the CBR contaminant by displaying realtime graphics on handheld computer implemented graphics devices, as well as host computers and distributed computers, showing current and predicted paths of plumes of the CBR plume, by estimating an initial source location of the unknown contaminant, calculating and displaying on graphic displays, an arrival time of at least one or more plumes associated with the CBR contaminant.

BRIEF DESCRIPTION OF THE DRAWINGS

FIG. 10A, FIG. 10B, FIG. 10C, FIG. 10D, FIG. 10E, FIG. 10F, FIG. 10G, FIG. 10H and FIG. 10L illustrate eight different plumes computed 20 minutes after an $SF_6$ trial release over downtown Los Angeles using the same input winds and weather.

FIG. 11A, FIG. 11B, FIG. 11C and FIG. 11D illustrate plume envelope construction schematically at a particular time after the contaminant release begins.

DETAILED DESCRIPTION OF THE INVENTION

Figure 1:
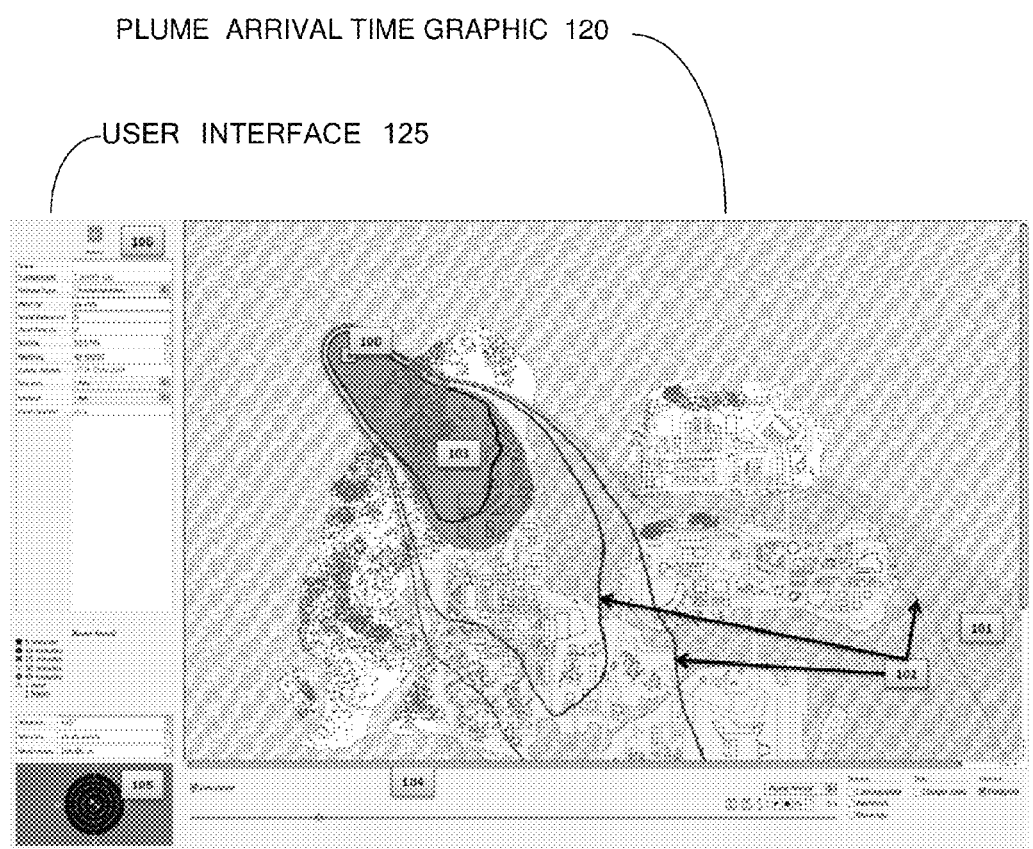
FIG. 1 illustrates a graphic depiction of CT-ANALYST Plume Arrival Time Graphic 120.

Preferred exemplary embodiments of the present invention are now described with reference to the figures, in which like reference numerals are generally used to indicate identical or functionally similar elements. While specific details of the preferred exemplary embodiments are discussed, it should be understood that this is done for illustrative purposes only. A person skilled in the relevant art will recognize that other configurations and arrangements can be used without departing from the spirit and scope of the preferred exemplary embodiments. It will also be apparent to a person skilled in the relevant art that this invention can also be employed in other applications. Further, the terms "a", "an", "first", "second" and "third" etc. used herein do not denote limitations of quantity, but rather denote the presence of one or more of the referenced items(s).

DEFINITIONS

Source: A source 100 (see FIG. 1) is defined as a location where an environmental hazard (e.g. chemical, biological or radiological agents) release was observed, or a potential release point. A source 100 has properties such as its georeferenced location, release time, release type (continuous, instantaneous), and the type of agent.

Hazard Area Footprint: The hazard area footprint 101 (see FIG. 1) is the largest area downwind from the source 100 that could be affected by the contaminant. A small "safety radius" is also included upwind from the source 100. The display of the hazard area footprint 101 is not time dependent and is generated from the position of the release point of the source 100, using CT-ANALYST's fast and accurate libraries to capture the effects of terrain and buildings on the wind-borne contamination.

Plume: The display of the plume 103 shows the hazard area footprint 101 downwind of the source 100. It is time dependent, showing the evolution of the region contaminated by a source 100. The maximum area of the plume 103 is always less than or equal to the area of the hazard area footprint 101.

First Exemplary Embodiment

Referring to FIG. 1, FIG. 2A FIG. 2B, FIG. 3, FIG. 4, FIG. 5, FIG. 6A and FIG. 6B, in accordance with a first exemplary embodiment, a plume arrival time calculation method 230, a plume arrival time display generation method 340 and a plume arrival time operational use method 450 are implemented in a computer readable and executable programs and stored in a computer writable and/or executable medium, such as computer usable medium 1302 and/or memory 508, and executed on a computer system 500 (hereafter the "system 500"). The method 230, the method 340, and the method 450 synergistically and automatically display the source 100, calculate and display the hazard area footprint(s) 101 and calculate and display the plum 103, and calculate the plume 103 arrival time(s).

Plume Arrival Display:

Referring again to FIG. 1 and FIG. 3, the plume arrival time display generation method 340 efficiently displays the following information about an environmental contaminant from a chemical, biological or radiological agent: (1) the hazard area footprint 101; (2) a time-dependant plume 103; and (3) perimeters 102 depicting the predicted time when the contaminant will reach that region within the hazard area footprint 101. Within this display, a user can manipulate the time 104 to quickly get an estimate of the extent of a contaminant release.

The display of the plume 103 that CT-ANALYST generates allows the user to instantaneously view this display and the display of the plume 103 can be manipulated in real-time, as the information about a contaminant is refined. The elements that make up this display will be discussed in detail below.

Figure 2A:
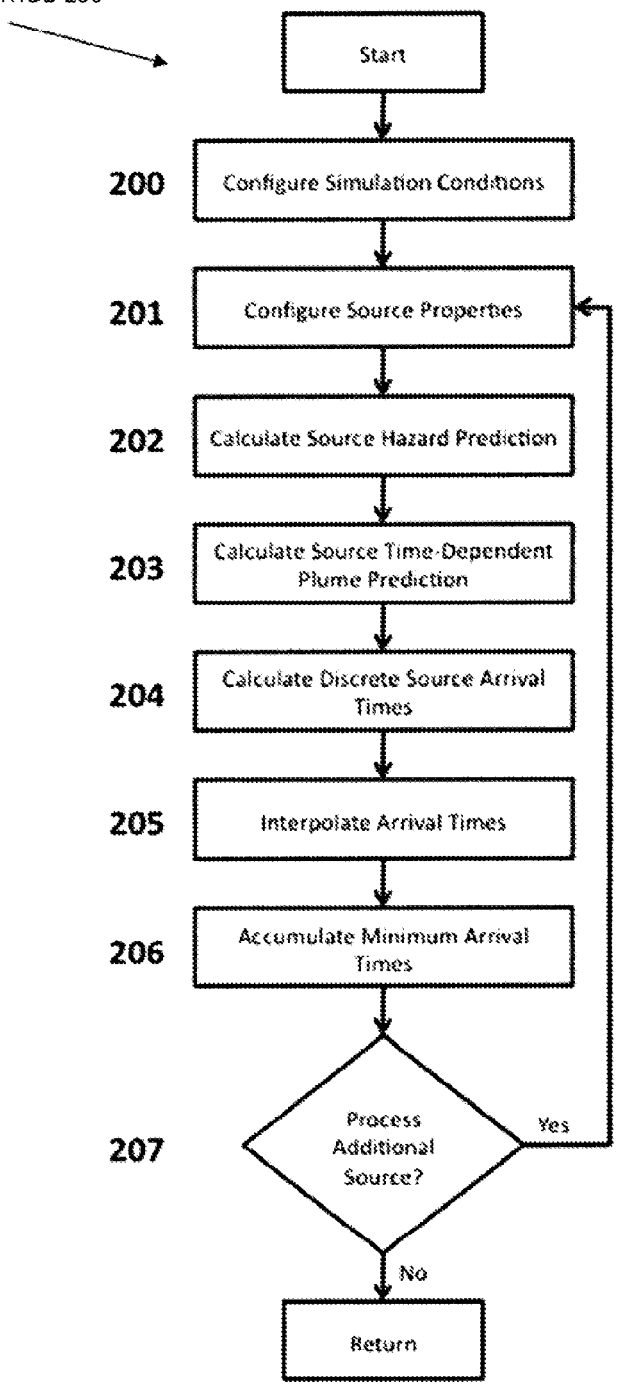
FIG. 2A and FIG. 2B illustrate calculation of Plume Arrival Time.
Figure 2B:
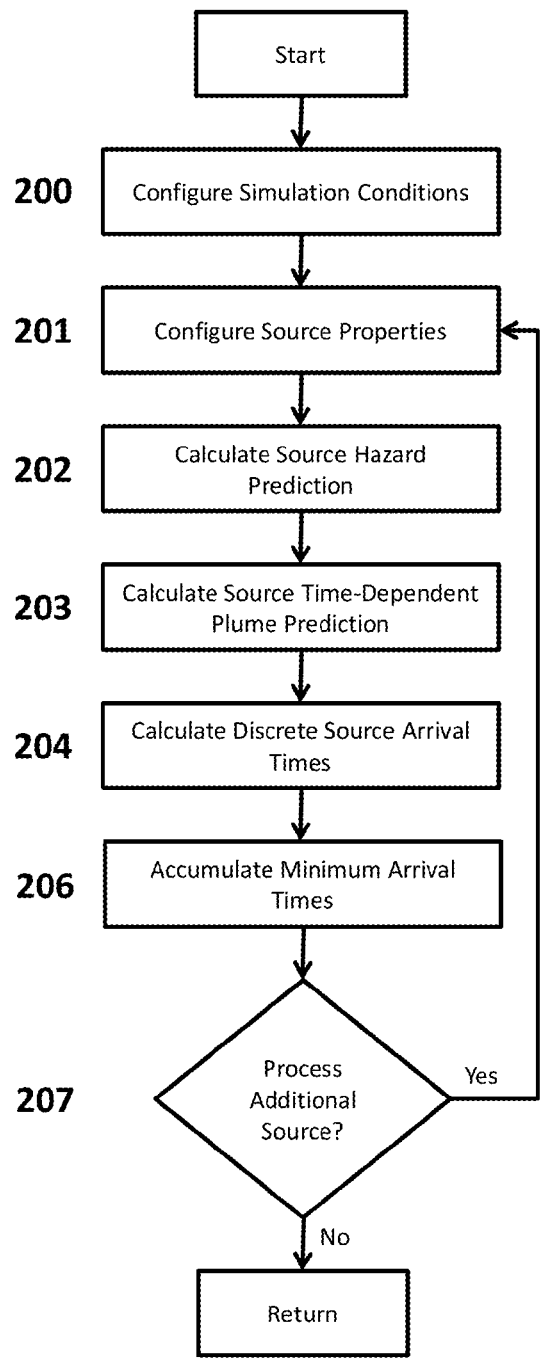
Figure 3:
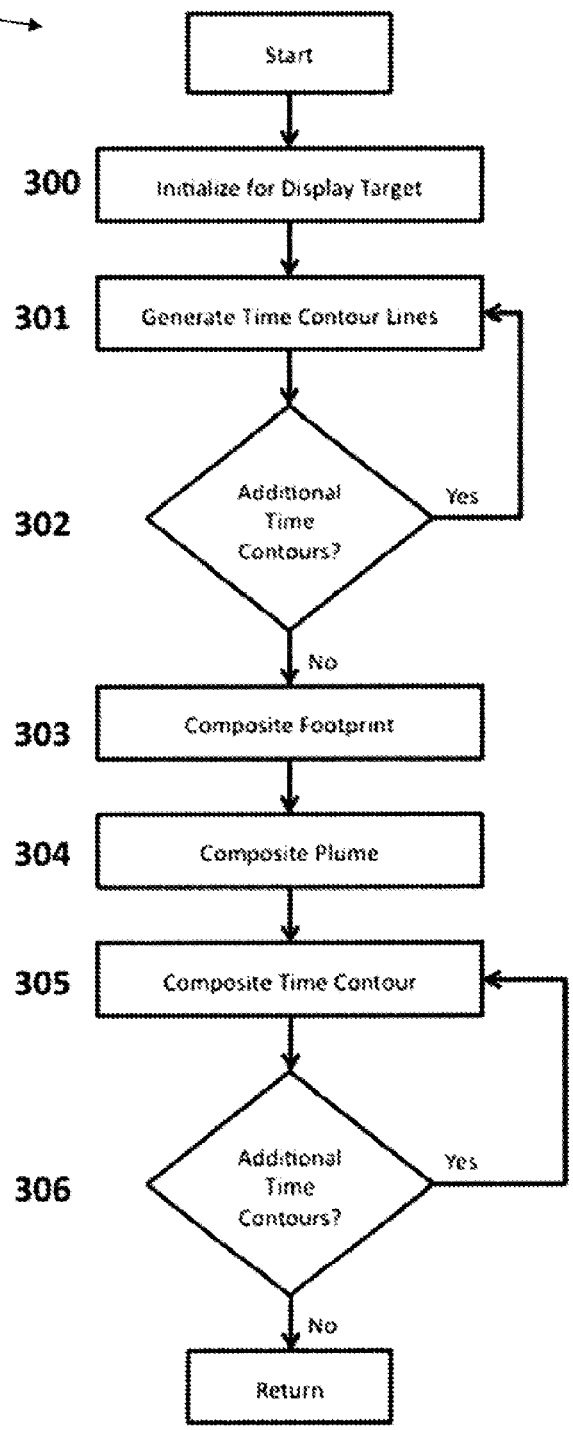
FIG. 3 illustrates generation of Plume Arrival Time Display.

Calculating Plume Arrival Element:

Referring to FIG. 2A, FIG. 2B, and FIG. 3, the display of the plume 103 has two main components: (1) the calculation of the arrival time for a contaminant plume 103 (see FIG. 2A and FIG. 2B) using the plume arrival time calculation method 230; and (2) the generation of the arrival time display using the plume arrival time display generation method 340 (see FIG. 3).

Referring to FIG. 2A and FIG. 2B, the plume arrival time calculation method 230 configures the plume simulation 200 in a configuration operation. This operation includes loading environmental data 550 such as terrain, building geometries, land use, weather conditions from meteorological sensor(s) 570 or forecasts, time, data gathered from experiments conducted in the field or wind tunnels, and the specification of boundary conditions for the simulation. Depending on the simulation, this data may only need to be reinitialized after a significant change in environmental conditions. Then source properties data 518 are specified by the configure source properties 201 operation. These source properties data 518 can include the mass/mass flow rate of the source 100, the type of release (continuous, instantaneous, etc), the source 100 location, the type of agent, time of release and other relevant properties.

Referring to FIG. 1, FIG. 2A, FIG. 2B, FIG. 5, these source properties data 518 parameters and other parameters, such as environmental data 550 are stored in memory 508 (where memory 508 includes a dynamic repository 510 having a plurality of repositories R90, R91, R92, R93, R94 through Rn) the source 100, the hazard area footprint 101, plume 103, and arrival time are computed. The hazard area footprint 101 for each source 100 is predicted by the calculate source hazard prediction 202 operation and is stored as a 2-D array "source hazard prediction" data into a data structure (which can be the dynamic repository 510 or one of a plurality of algorithms (including simulation algorithms), such as A1, A2, A3 up to An, which reside in an algorithm unit such as algorithm unit 530) to accumulate the total hazard area by all sources within the domain; this 2-D array of source hazard prediction data will be called by a subroutine to be used in generate a composite hazard area footprint in the composite footprint 303 operation, see FIG. 3. The prediction data, as well as any other plurality of data may be in data structures to include two dimensional, three dimensional, four dimensional and greater multi-dimensional data arrays and/or data structures. The data structure is comprised of a collection of values associated with a position in the domain to denote if the contaminant reached that location. These data are stored in memory in a data structure format, so as to be called/retrieved and used in the execution by the computer processor in various operations. In a similar manner the time dependent plume 103 is calculated and stored as a 2-D array of "time dependent plume prediction" data at operation calculate source time dependent plume prediction 203; this 2-d array of time dependent plume prediction data will be called later for use in generate the composite plume in operation 304 (see FIG. 3).

Referring to FIG. 2A and FIG. 2B, and further according to the first exemplary embodiment, then arrival time is calculated by the plume arrival time calculation method 230 in operation calculate discrete source arrival times 204 operation(s) and stored as a 2-D array of discrete Source Arrival Time data for each source 100; this 2-D array of discrete Source Arrival Time data will be called later for use in generating time contour lines in operation 301 and will also be called to be used to generate the composite time contour in operation 305 (see FIG. 3).

Second Exemplary Embodiment

According to a second exemplary embodiment, referring to FIG. 2A, the computation of arrival time varies depending on the simulation selected. If the simulation calculates arrival time for several times (e.g. 5, 15 and 30 minute plume(s) 103), the results will have to be interpolated to obtain the intermediate values determined in the interpolate arrival time(s) 205 operation. Therefore, in the second exemplary embodiment, the interpolate arrival time 205 operation is optional (see FIG. 2B), depending on the simulation selected. For example a Computational Fluid Dynamics (CFD) simulation which runs for an hour with a small time step interval can merely record the time a contaminant reached that location in the domain as the simulation progresses. For locations of interest within the simulation, if the minimum time it took for the contaminant to reach that position is lower than the currently recorded minimum time value, the new lower minimum time is recorded in the accumulate minimum arrival time(s) 206 operation of the plume arrival time calculation method 230. The data structure for arrival time is comprised of a collection of times associated with a position in the domain to represent the minimum time it took for a contaminant to reach that location. If there are additional sources this process continues until all three components of the Plume Arrival Display are computed in the process additional source 207 operation.

Further, according to the second exemplary embodiment, the data structures for hazard area footprint 101, plume 103 and arrival time do not have to be separate and may be interleaved or use encoded values. For example the arrival time data structure could be used for all three components where a positive value denotes the hazard area and arrival time while plumes 103 are represented by values less than or equal to the time after the source 100 releases.

Continuing with the First Exemplary Embodiment:
Displaying Plume Arrival Element:

Referring to FIG. 1 and FIG. 3, once the initial conditions of at least calculating the arrival time for a contaminant plume and the generation of the arrival time display have been specified, the Plume Arrival Display is calculated in the plume arrival time display generation method 340; thus, FIG. 3 depicts the overall procedure to generate the Plume Arrival Time Display. First, the data structure for the display is initialized in an operation called Initialize for Display Target 300. This data can vary depending on the display target. In exemplary embodiments, when the display type is a graphics image data structure, it can include the display geometry, coordinate system, color depth, and other relevant display properties. This contrasts with a Geographic Information System ("GIS") data structure, where the data could be in a geo-referenced polygon encoded in an Extensible Markup Language ("XML") format. Further in exemplary embodiments, display targets include graphics displays, GIS-compatible data structures (Keyhole Markup Lnguage ("KML"), Environmental Systems Research Institute, Inc.'s Shapefile geospatial vector data format ("ESRI Shapefile")), and raster image files (georeferencing Tagged Image File Format ("GeoTIFF"), Portable Network Graphics ("PNG"), Joint Photographic Experts Group ("JPG")).

Referring to FIG. 3, once the target has been specified, time contour lines are generated from the arrival time data structures in the generate time contour lines 301 operation. Time contours can be generated for any valid time within the simulation, but a typical display will depict time contours with an increasing time interval (e.g. 5, 15, 30, and 60 minute arrival times). This process continues until all time contours have been calculated, see the additional time contours 302 decision diamond in FIG. 3.

Figure 5:
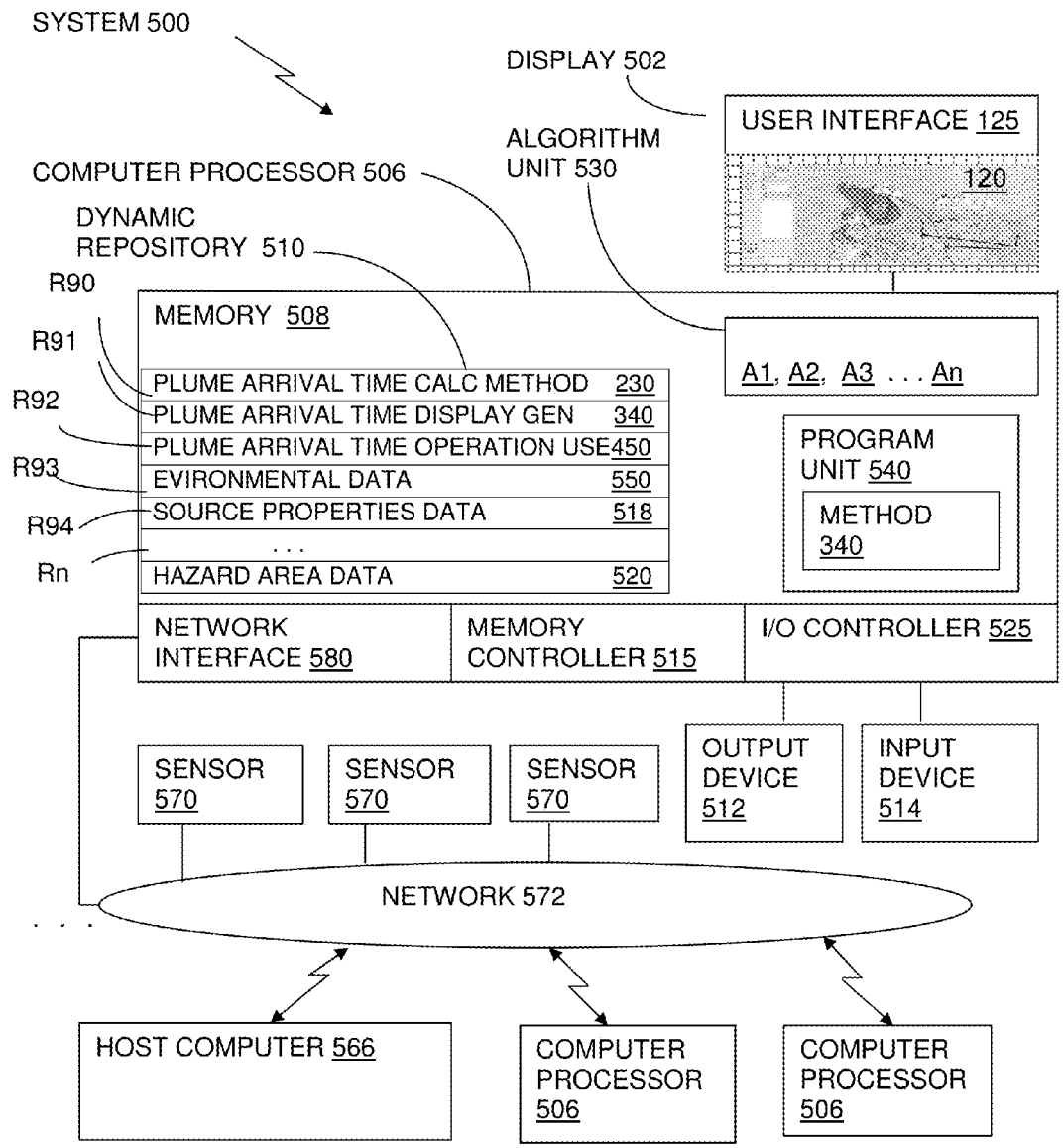
FIG. 5 illustrates a Computer Processor executing operations of calculation of Plume Arrival time and generation of Plume Arrival Time Display.

Referring to FIG. 3 and FIG. 5, for the various components of the plume arrival display, an intermediate data structure is generated that is then sent to the display target. For the case where the final display is a computer monitor, such as display 502, the data structure can be a raster image comprised of color information or a set of polygons which represent each element of the display. The data structures for each of the Plume Arrival elements are not exclusively raster or vector and can be of different times depending on the requirements of the display 502. These data structures are then composited with the hazard area footprint 101 forming the base layer in the composite footprint 303 operation, followed by the composite plume 304 operation and Arrival Time Contours formed in the composite time contour 305 operation, respectively. These various compositing operations can take place on the CPU, i.e., computer processor 506, on dedicated graphical hardware or a mixture of the two. Multiple time contours are then processed and composited to the screen of the display 502 via the additional time contours 306 decision diamond. A similar process is followed for GIS displays or raster files where the output is typically sent to a storage device or over a network 572 connection for use by a separate program, where the network 572 can be an electronic communications and/or a telecommunications network. For example sending a PNG image via an email attachment or viewing the Plume Arrival Time as an overlay in a GIS Program.

Figure 4:
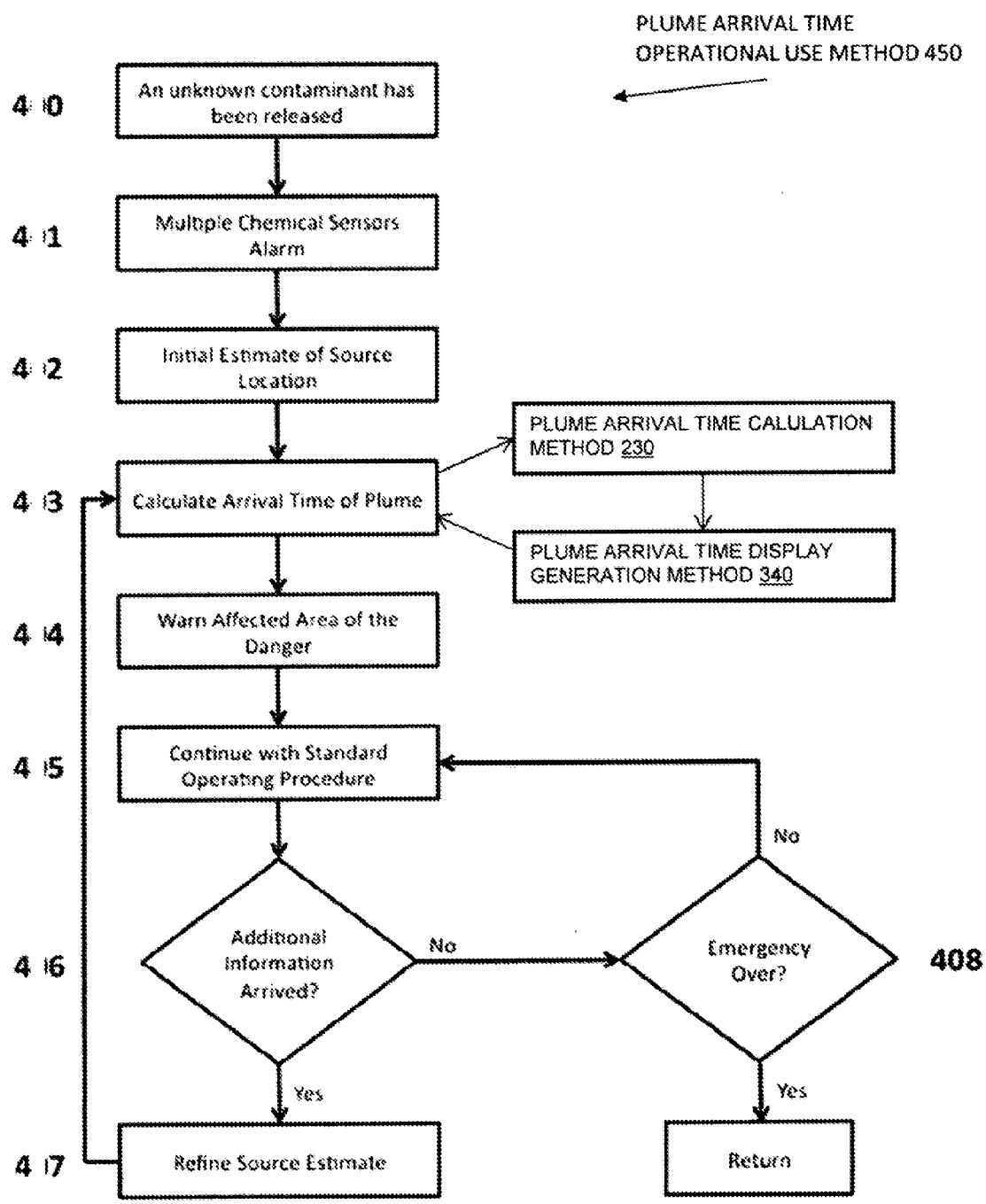
FIG. 4 illustrates Operational Use of Plume Arrival Time.

Plume Arrival Time Operational Use Method 450:

Referring to FIG. 4 and FIG. 5, in an exemplary embodiment, the plume arrival time operational use method 450 is illustrated. This exemplary embodiment of an operational environment involves a chlorine leak from a tanker in a railroad yard characterized initially as: an unknown contaminant has been released 400". Shortly after the release, several chemical sensor(s) 570 downwind from the source 100 cause an alarm indicating that chlorine was detected, as illustrated in the multiple chemical sensors alarm 401 operation.

Referring again to FIG. 4 and FIG. 5, an operator who is trained in the use of CT-ANALYST uses the backtrack capability of CT-ANALYST to give an estimate of the source 100 location and then adds a source 100 to an estimate of the downwind region affected in the initial estimate of source location 402 operation. Looking at the display 502, the user notes that for the given conditions a nearby industrial park will be affected in 10 minutes and a commercial area that is heavily populated during the day will be affected within the hour based on the calculate arrival time of plume 403 operation. Following standard operating procedures (SOP), the operator uses reverse 911 to inform the industrial park and the commercial district to evacuate the area specifying the evacuation route to avoid the contaminant 404. Hazardous Materials workers ("HAZMAT") are dispatched to look for the source 100 release and are directed to wear protective gear if entering the hazard area as designated in the hazard area footprint 101 or avoid it completely, based on the continue with standard operating procedure 405 operation.

In the meantime the operator obtains a detailed report from the railroad yard about the contaminant, based on the additional information arrived 406 operation. The user updates the information about the source 100 estimate based on activation of the refine source estimate 407 operation and reruns the Plume Arrival Calculation in calculate arrival time of plume 403 operation. Because the change in the hazard area footprint 101 was minor, the SOP continues and HAZMAT begins the process of stopping the leak and beginning cleanup. This process of refining the source 100 estimate in the refine source estimate 407 operation and following the SOP continues until the emergency has been mitigated, based on the emergency over 408 operation decision diamond.

The time it takes to calculate the hazard area footprint 101, plume 103, and arrival time can vary depending on the selection of simulation algorithm. If a traditional simulation is utilized the data for these components of the plume arrival time display may be calculated as the simulation progresses. However this can take a relatively long time and require a significant amount of computing power to calculate a display in a timely manner. CT-ANALYST's approach of using pre-calculated data allows these displays to be calculated almost instantaneously. Furthermore the algorithm that CT-ANALYST employs allows these elements to be calculated in any order or in parallel depending on the capabilities of the underlying computer system to further decrease the time to answer or increase the displayed resolution.

The plume arrival time display, based on the plume arrival time display generation method 340 can be generalized into a display consisting of components for an overall hazard footprint area 101 or detection area, a time dependent area, and arrival time. These displays can depict information for upwind and downwind directions and do not necessarily depend on information about a source 100. This method can be used to depict arrival times for when a particular health effect occurs, sensor 570 coverage, site protection, estimating source 100 location from reports, and the estimation of contaminant spread from sensors 570 which have indicated alarmed conditions.

The health effects variant of this display would consist of the following elements: the overall area affected by the contaminant, a time dependent component depicting the health effects, and the health effect arrival time that denotes how much time one would have to be within that boundary to show symptoms of a particular health effect. There are additional variants for health effects such as the replacing the hazard area footprint 101 with the maximum area where a particular health effect would take place.

Referring again to FIG. 5, in accordance with exemplary embodiments, the system 500 includes a computer processor 506 (hereafter "the computer processor 506") communicatively coupled to and/or communicatively coupling either externally or residing inside of the computer processor 506 a plurality of network interface controllers, input/output controllers, input devices and output devices, such as a network interface 580, a memory controller 515, an input/output controller 525 (hereafter "the I/O controller 525"), an input device 514, an output device 512, and a display 502, where the display 502 displays a user interface 125. In exemplary embodiments, software application packages including special purpose algorithms or any other commercially available software application packages (such as CT-ANALYST) can be accessed and exercised interactively by a user using the computer processor 506, either locally or remotely over a network 572.

Again referring to FIG. 5, in accordance with exemplary embodiments, the network interface 580 communicatively connects the computer processor 506 to a network 572, where a plurality of client side, server side and/or user networked devices and/or platforms reside, interact and operate communicatively over the network 572. The network 572 can be a wide area communications network, including an Internet or an extranet or the network 572 can be a local area network, including an intranet, including wired or wireless communications capabilities. These networked devices, platforms and/or systems can include host computers, such as a host computer 566 (which may also contain one or more of the computer processor 506); these devices and systems can include storage devices, such as tape drives, thumb drives, and disc drives, operating individually or in storage library farms; in exemplary embodiments, a plurality of storage devices can include a device such as one or more of a storage and or sensors, such as sensor(s) 570. These networked devices can also incorporate a plurality of devices, such as the computer processor 506.

Again referring to FIG. 5, in accordance with exemplary embodiments, the input device 514 can be at least one or more of a mouse, a keyboard, a touch screen terminal, a light pen wand, a joystick, a thumbwheel, a copier system or machine, a hardcopy paper scanner system or machine, a microphone or an electronic and/or a radio frequency scanning device (including Radio Frequency Infrared Detector ("RFID")).

Figure 6A:
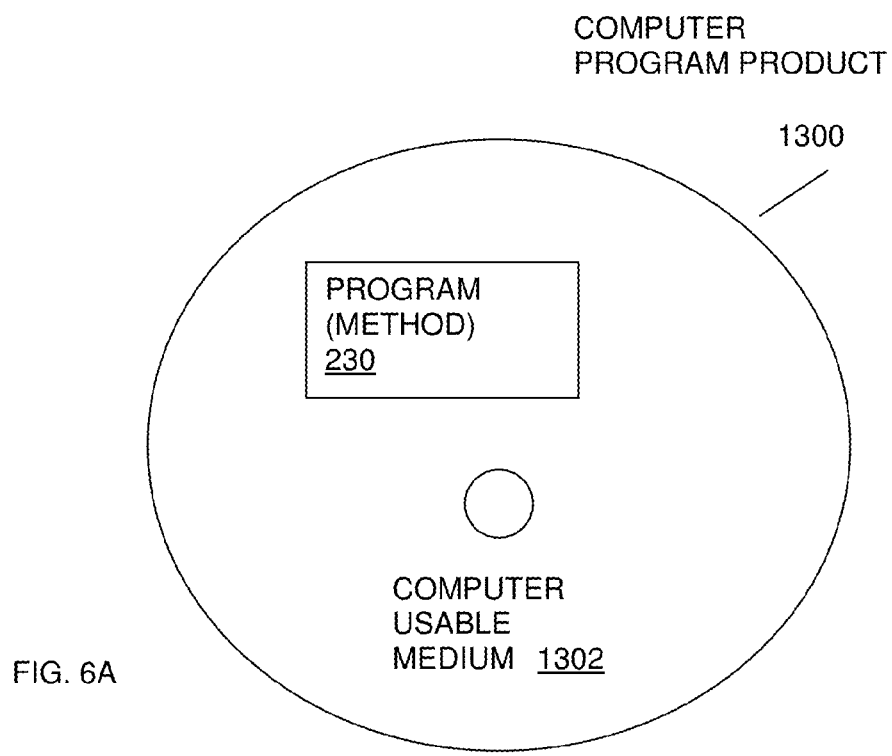
FIG. 6A illustrates an exemplary computer readable and computer executable medium containing a program product including program logic of the plume arrival time calculation method 230.
Figure 6B:
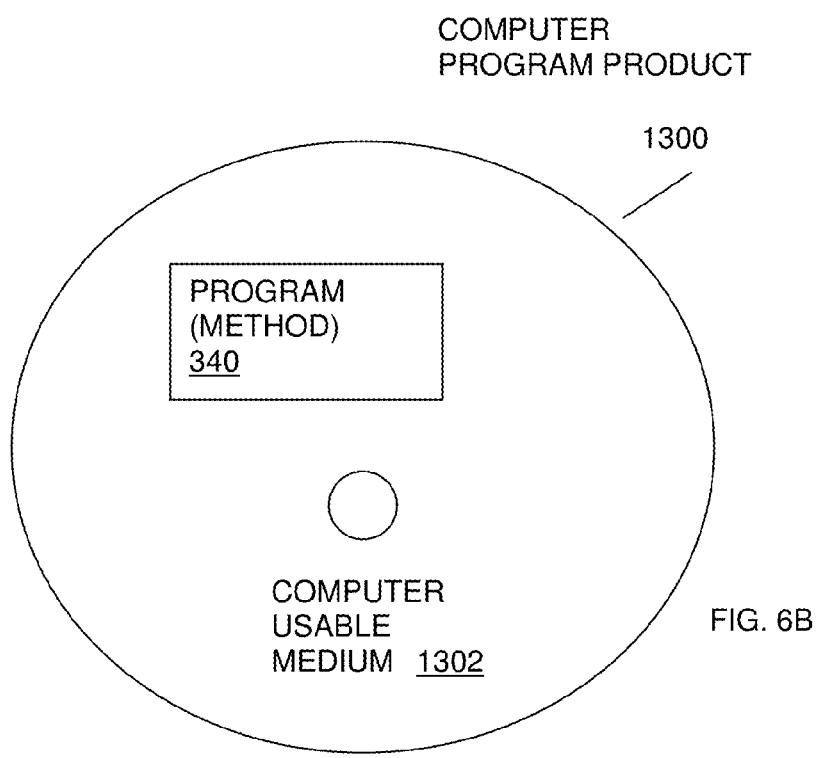
FIG. 6B illustrates an exemplary computer readable and computer executable medium containing a program product including program logic of the plume arrival time display generation method 340.
Figures 7A, 7B:
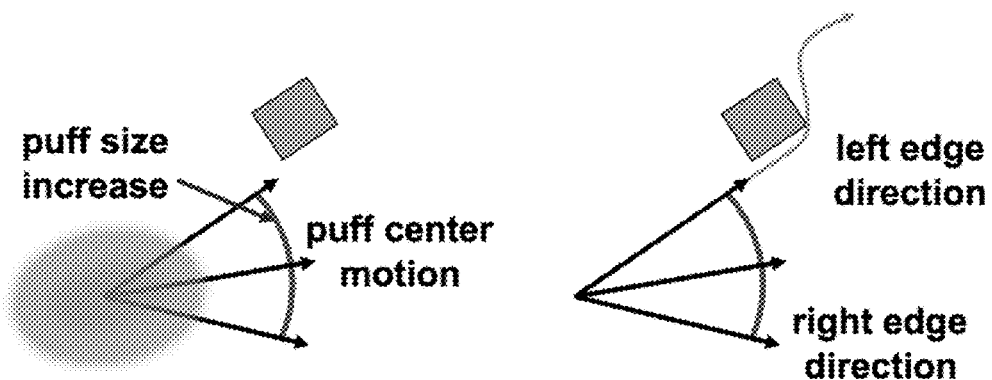
FIG. 7A illustrates Gaussian puff methods on the left use the wind velocity at the puff center to determine where the center moves and use the fluctuations, represented by the arc(s) and to determine how much the puff spreads during a timestep.
FIG. 7B illustrates a zig-zag line showing how the left plume edge is deflected around a building.
Figure 8:
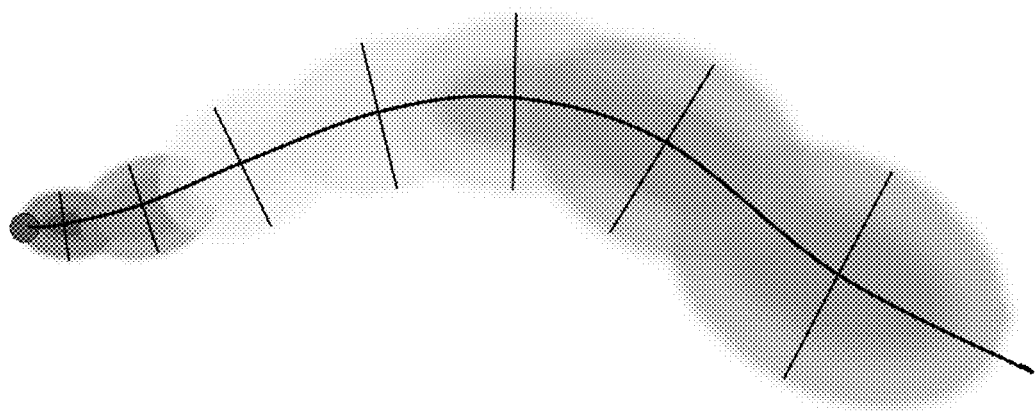
FIG. 8 illustrates the beginning of the detailed solution procedure for Gaussian puff models.
Figure 9:
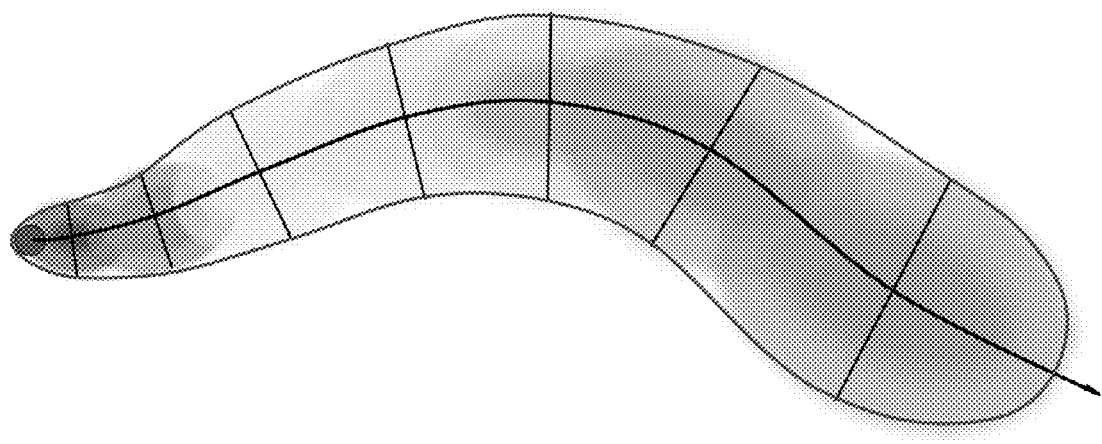
FIG. 9 illustrates how this Gaussian puff information is used to compute a hazard area, indicated by the red line, for the overall plume.
Figure 12:
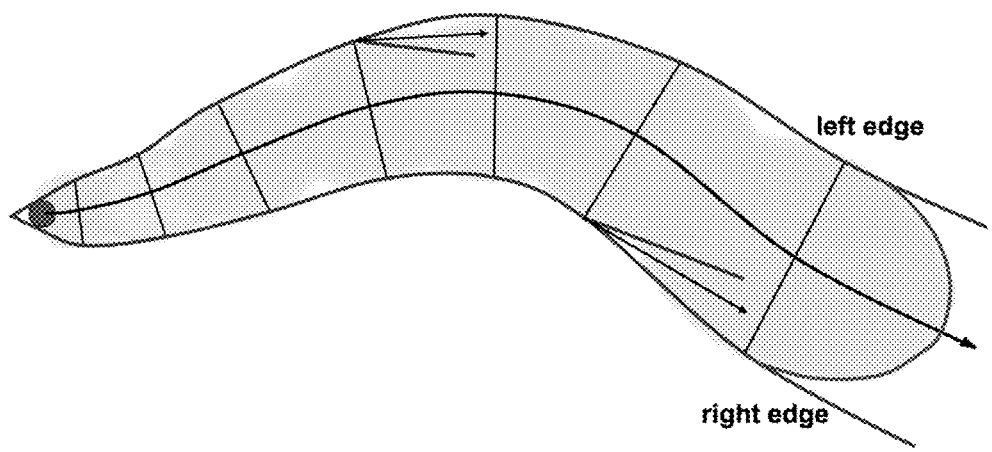
FIG. 12 illustrates the result of computing left and right plume edges and dispersion of a contaminant.
Figure 13:
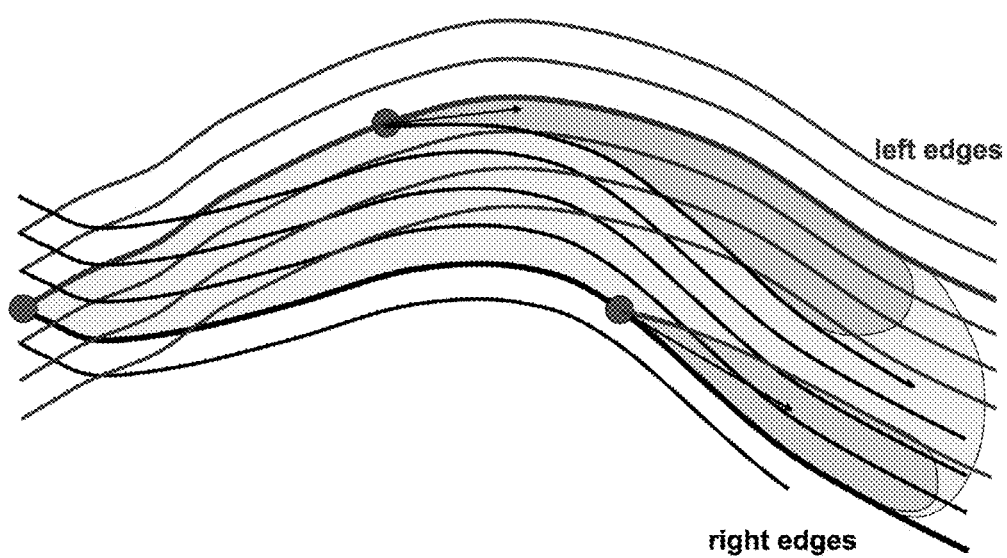
FIG. 13 illustrates left edges and right edges limiting plume edge paths.
Figure 14A:
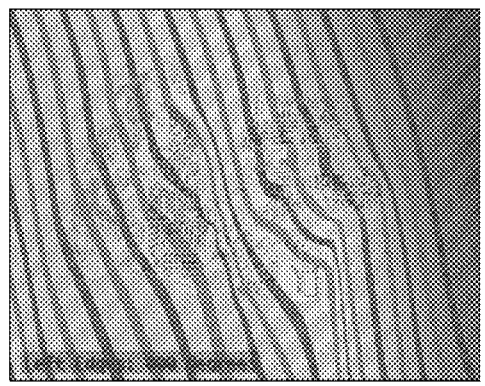
FIG. 14A and FIG. 14B illustrate left edge and right edge DISPEERSION NOMOGRAF contours for a fictitious island kingdom called Atlantis.
Figure 14B:
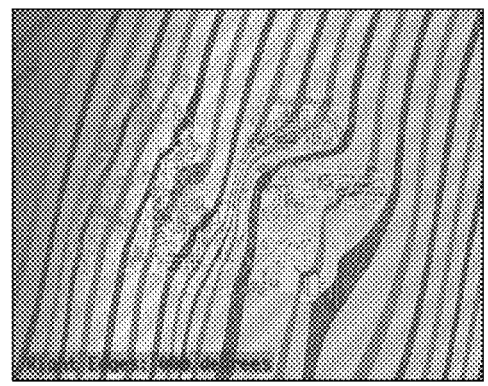
Figure 15:
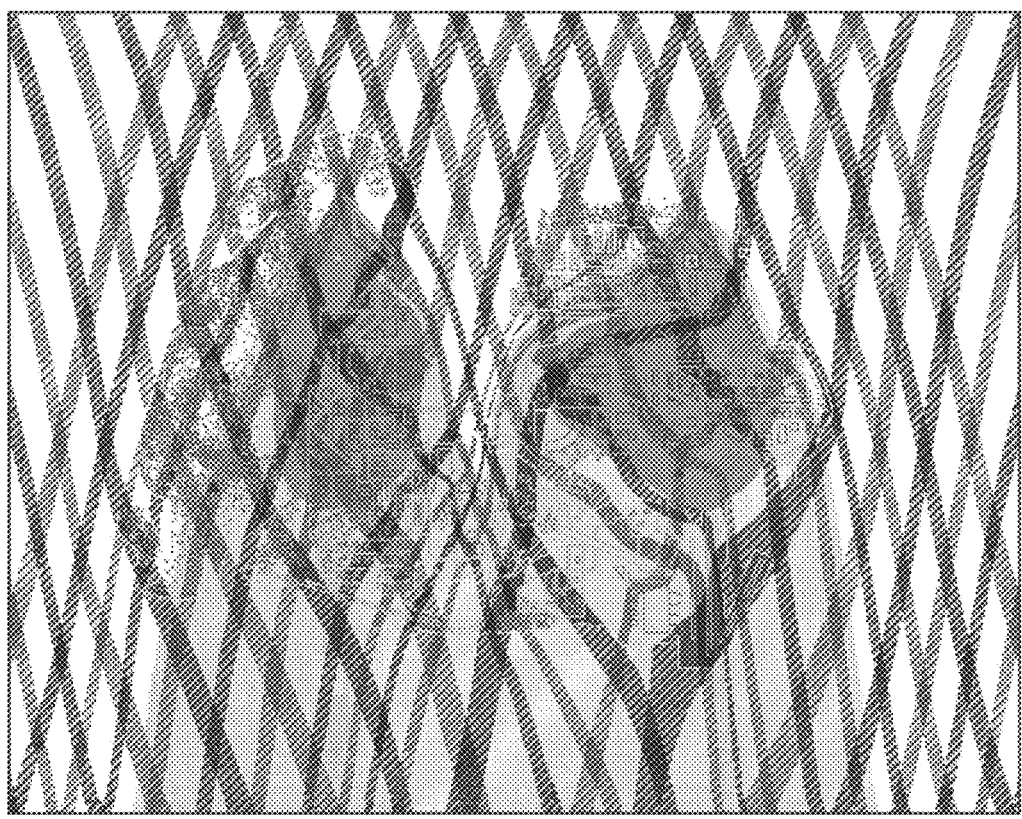
FIG. 15 illustrates two distinct plume envelopes from CT-ANALYST which are shown in relationship to the underlying nomograf edge contours.
Figure 16:
FIG. 16 is a CT-ANALYST full screen shot showing contaminant density contours, the contamination footprint, and evacuation routes overlaid on a Washington D.C. city map.
Figure 17A:
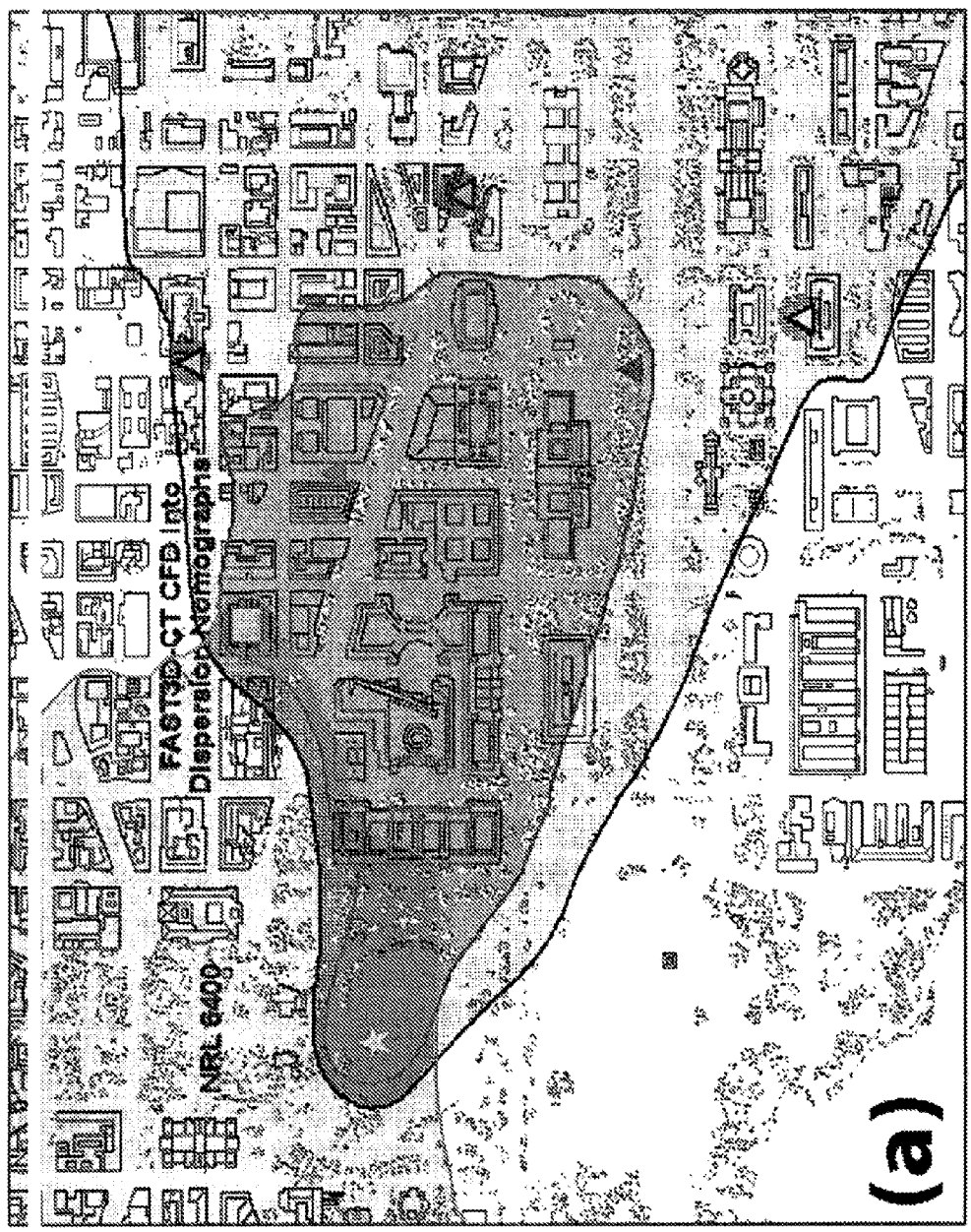
FIG. 17A and FIG. 17B illustrate how DISPEERSION NOMOGRAFS in CT-ANALYST capture building aerodynamics.
Figure 17B:
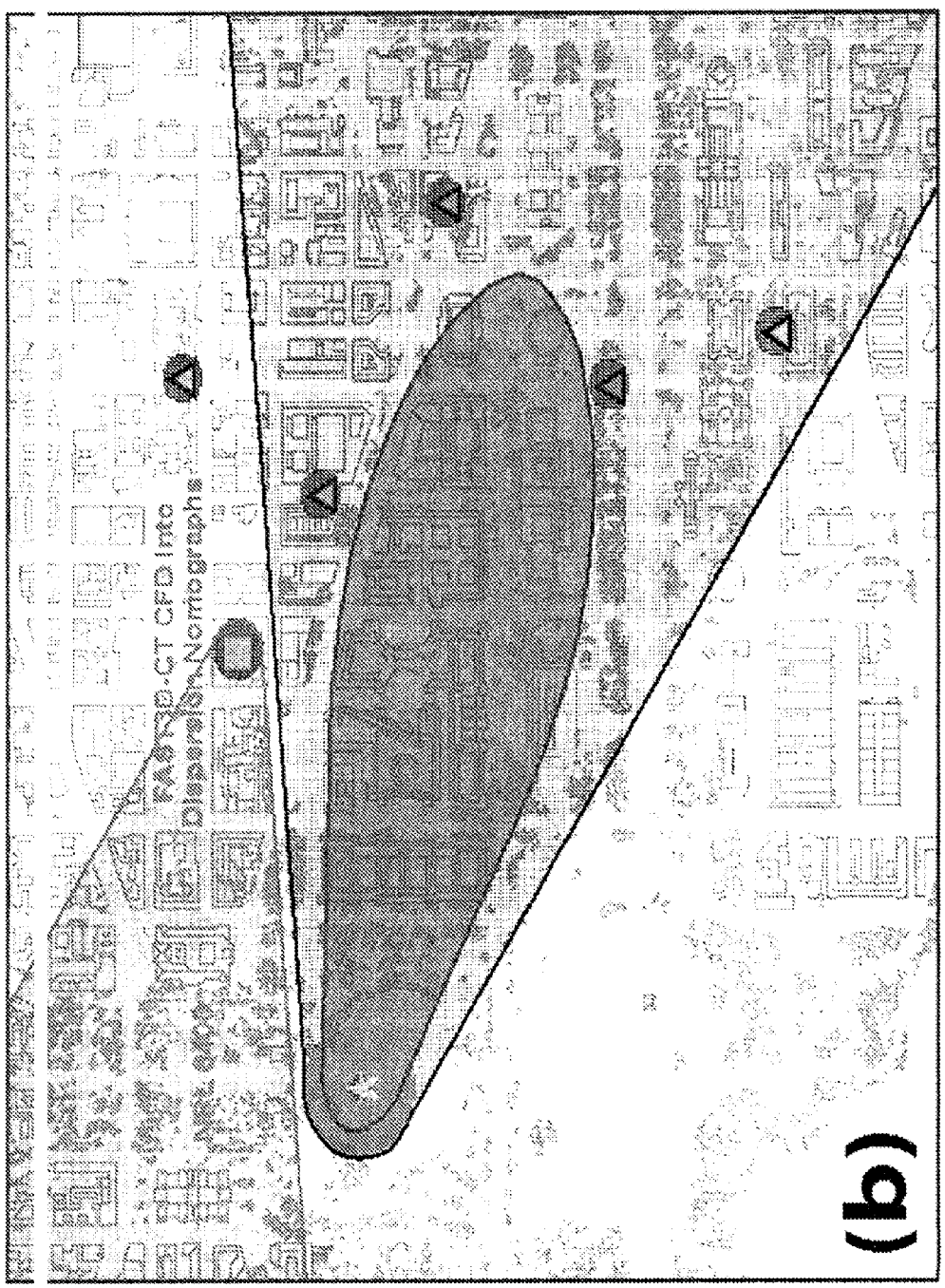

In exemplary embodiments, the system 500 and the method 230, the method 340, and method 450, illustrated in FIG. 5, FIG. 6A and FIG. 6B respectively, can be implemented in software, firmware and/or hardware or any combination of each. According to exemplary embodiments, the method 230, the method 340, and method 450 are implemented in software, as executable program code (such as program 340 and/or program 230) which comprises an ordered listing of a plurality of computer executable instructions for implementing logical functions, and the method 230, the method 340, and method 450 are executed by either special or general purpose digital computers including a personal digital assistant ("PDA"), a personal computer, a workstation, a minicomputer or a mainframe computer as implemented in computer processor 506, in accordance with exemplary embodiments.

Referring again to Further in accordance with exemplary embodiments, the system 500 is implemented with a general purpose digital computer designated as the computer processor 506; however, the system 500 has been implemented on any number of specific hand-held personal computers, such as smart phones, IPADs, and laptops, as well as, larger computers including desktops, towers, workstations and can be implemented on larger computer systems including minicomputers and mainframes, as suggested in FIG. 5, illustrating a host computer 566. The computer processor 506 is a hardware device for executing software implementing programs of the method 230, the method 340, and method 450, including any and all associated algorithms and/or called subroutines. The computer processor 506 can be any custom made or commercially available, off-the-shelf processor, a central processing unit (CPU), one or more auxiliary processors, a semiconductor based microprocessor, in the form of a microchip or chip set, a macroprocesssor, graphic processors or generally any device(s) for executing software and/or firmware instructions. The system 500 when implemented in hardware can include discrete logic circuits having logic gates for implementing logic functions upon data signals, or the system 500 can include an application specific integrated circuit (ASIC).

Referring to FIG. 5, in accordance with exemplary embodiments, the computer processor 506 further includes a memory 508 (hereafter "the memory 508"). Residing in the memory 508 are a program unit 540 (hereafter "the program unit 540") and a dynamic repository 510 (hereafter "the dynamic repository 510"), where the dynamic repository 510 can be a dynamic random access memory (DRAM). Residing in the dynamic repository 510 are a plurality of repository entry locations R90, R91, R92, R93, R94, and R95 up to and including Rn, where Rn theoretically represents an infinite number of repository entry locations limited only by known physical and/or virtual memory capacity. Thus, each repository entry location R90 up to Rn can hold, store and/or save a plurality of information and/or data including algorithms and program data, including the method 230, the method 340, and method 450 represented as being stored in repository entry location R90, R91 and R92, respectively.

In accordance with exemplary embodiments, referring to FIG. 5, environmental data 550 is held in repository entry location R93.

Further in accordance with exemplary embodiments, referring to FIG. 5, source properties data 518 is held in repository entry location R94.

Referring again to FIG. 5, in accordance with exemplary embodiments, hazard area data 520 are stored in repository entry location R95. These groups of data, algorithms (i.e., simulation algorithms) and/or program information can be easily, automatically, and programmatically accessed/called and exercised by computer processor 506, resulting in generating plume arrival times and hazard area footprint(s) 101 displayed on display 502, so as to quickly get an estimate of the extent of a contaminant release.

In addition, a plurality of other data and/or algorithms (such as simulation algorithms) and information may be called and entered into the repository entry locations R90 through Rn. The plurality of other data and or algorithms can include: (1) elements of environmental data 550, such as terrain, building geometries, land use, weather conditions from meteorological sensors or forecasts, time, data gathered from experiments conducted in the field or wind tunnels, and the specification of boundary conditions for the simulation; (2) elements of source properties data 518, which further include: the mass/mass flow rate of the source, the type of release (continuous, instantaneous, etc), its location, the type of agent, time of release and other relevant properties; (3) data structure values comprised of a collection of values associated with a position in the domain to denote if the contaminant reached that location; (4) intermediate values derived from calculations and simulations; (5) CFD simulation algorithm (A1); and (6) interpolation algorithm (A2), etc.

Referring again to FIG. 5, in accordance with exemplary embodiments, the memory 508 further includes an algorithm unit 530. Residing in the algorithm unit 530, is a plurality of algorithms such as an algorithm A1, an algorithm A2, an algorithm A3, an algorithm A3, up to and including an algorithm An, where the algorithm An theoretically represents an infinite number of algorithms limited only by known physical and/or virtual memory capacity. In exemplary embodiments, algorithm A1 can be a CFD simulation algorithm (A1); and the algorithm A2 can be an interpolation algorithm (A2). These algorithms can be in the form of one or more formulas, applets, programs, routines, sub routines, macro programs and/or micro programs and/or any combination of such programs, applets, formulas, routines and/or sub routines. In exemplary embodiments, these algorithms and/or formulas can represent either individual segments of knowledge base applications or standard known programming languages which are called and/or executed to create rapid predictions and models which enable active design of air transportation systems. These algorithms and/or formulas are called by programmatic operations of the method 230, the method 340, and method 450, either automatically or manually to perform computational and predictive tasks. Furthermore, these algorithms can be stored temporarily and/or permanently and/or semi permanently in the algorithm unit 530 or stored over the network 572 in any of the plurality of computers or storage devices, such as the sensor 570, host computer 566, computer processor 506 or in a repository (such as the dynamic repository 510) in the computer processor 506 or in any one or more of the computer processor memory 508. In exemplary embodiments, the plurality of algorithms and/or formulas can be downloaded programmatically over the network 572 or entered manually by way of the input device 514.

Referring to FIG. 5, FIG. 6A and FIG. 6B, in accordance with exemplary embodiments, residing in the program unit 540 is a plurality of computer readable and/or computer executable and/or computer writable media (such as a computer usable medium program product 1300) which contain a plurality of computer programs (such as program method 230, the program method 340, and program method 450), or algorithms and/or software applications, composing operations, instructions and/or procedures of the method 230, the method 340, and method 450 encoded as computer readable and computer executable program code, contained in the computer program product 1300. In exemplary embodiments, software in the program unit 540 includes a suitable operating system.

In exemplary embodiments, referring to FIG. 5, FIG. 6A and FIG. 6B, the memory 508 and the dynamic repository 510 and the plurality of storage devices can include any one of or a combination of volatile memory elements, including random access memory (i.e., including RAM, DRAM, SRAM and/or SDRAM) and non-volatile memory elements including read only memory (i.e., ROM, erasable programmable read only memory, electronically erasable programmable read only memory EEPROM, programmable read only memory PROM, and/or compact disc read only memory CDROM or FLASH memory or cache) magnetic tape, disk, diskette, cartridge, cassette and/or optical memory (see FIG. 6A and FIG. 6B). The memory 508 can have an architecture where various components are situated remotely from one another, but can be accessed by the computer processor 506, either directly and/or locally or logically through various communications buses or remotely over the network 572.

Referring to FIG. 1, FIG. 2A, FIG. 2B, FIG. 3, FIG. 4, FIG. 5, FIG. 6A and FIG. 6A, in accordance with a first exemplary embodiment, at an operation start 231 (hereafter "the operation 231"), the system 500 receives instruction from an operator or an individual user via either the input device 214 or an automatic programmatic wake up signal from the computer processor 506, which activates and initiates the computer executable program code implementing the either/or method 230, the method 340, and/or method 450. The method 230, the method 340, and/or method 450, upon activation, performs other operations from selection instructions received in the computer processor 506 from the input device 514, causing the method 230, the method 340, and/or method 450 to be executed by the computer processor 506 and in turn causing the computer processor 506 to perform operations and procedures and execute instructions including calling algorithms and software applications and executing the instructions in the algorithms and applications including mathematical calculations, analyses and determinations resulting in rapid predictions and models which enable active estimates of plume arrival time and hazard footprint area 101 displays.

Referring to FIG. 5, in accordance with the first exemplary embodiment, at the plume arrival time calculation method 230 operation, the system 500 receives instructions from an operator or an individual user via the input device 514 associated with computer processor 506, causing the computer processor 506 to perform operations and procedures including calculation of plume arrival time estimate(s).

In the first exemplary embodiment, the operations of the plume arrival time calculation method 230 includes the following operations:

Referring again to FIG. 1, FIG. 2A, FIG. 2B and FIG. 5, in accordance with the first exemplary embodiment, at an operation start 231, the program code of the method 230 executed by the computer processor 506 of the system 500 causes the computer processor 506 to initiate the plume arrival time calculation method 230, and execute configuration of the plume simulation by calling one or more appropriate simulation algorithms containing the configure simulation conditions 200 algorithm. This includes the loading of environmental data 550, such as terrain, building geometries, land use, weather conditions from meteorological sensors or forecasts, time, data gathered from experiments conducted in the field or wind tunnels, and the specification of boundary conditions for the simulation. Depending on the simulation, this data may only need to be reinitialized after a significant change in environmental conditions.

Again referring to FIG. 1, FIG. 2A, FIG. 2B and FIG. 5, in accordance with the first exemplary embodiment, at an operation configure source properties 201, the source's properties are then set within the simulation. These source properties data 518 (see FIG. 5) can include the mass/mass flow rate of the source, the type of release (continuous, instantaneous, etc), its location, the type of agent, time of release and other relevant properties.

Again referring to FIG. 1, FIG. 2A, FIG. 2B and FIG. 5, in accordance with the first exemplary embodiment, with the source properties data set and stored, the hazard area for each source is stored at the operation of the calculate source hazard prediction 202 operation.

Again referring to FIG. 1, FIG. 2A, FIG. 2B and FIG. 5, in accordance with the first exemplary embodiment, at an operation calculate source time dependent plume prediction 203, the time dependent plume is calculated and stored.

Again referring to FIG. 1, FIG. 2A, FIG. 2B and FIG. 5, in accordance with the first exemplary embodiment, at an operation calculate discrete source arrival times 204, the arrival time is then calculated for each source. The computation of arrival time varies depending on the simulation selected.

Referring again to the Second Exemplary Embodiment, if the simulation calculates arrival time for several times (e.g. 5, 15 and 30 minute plumes), the results will have to be interpolated to obtain the intermediate values.

The interpolation operation is optional, depending on the simulation selected. For example a CFD simulation that runs for an hour with a small time step interval can merely record the time a contaminant reached that location in the domain as the simulation progresses.

For locations of interest within the simulation, if the minimum time it takes for the contaminant to reach that position is lower than the currently recorded value, the new lower minimum time is recorded at operation accumulate minimum arrival times 206.

The data structure for arrival time is comprised of a collection of times associated with a position in the domain to represent the minimum time it took for a contaminant to reach that location. If there are additional sources this process continues as directed by decision operation diamond process additional source? 207 operation, until all three components of the Plume Arrival Display are computed.

Again referring to, FIG. 1, FIG. 2A and FIG. 5, in accordance with the second exemplary embodiment, at an operation interpolate arrival times 205, the results of operation calculate discrete source arrival times 204 will have to be interpolated to obtain the intermediate values.

Further, in the first exemplary embodiment, the operations of the plume arrival time display generation method 340 generates plume arrival time displays. FIG. 3 illustrates the operations which generate the Plume Arrival Time Display; FIG. 3 is associated with the following operations:

Referring FIG. 3 and FIG. 5, in accordance with the first exemplary embodiment, at an operation start 341, the program code of the method 340 executed by the computer processor 506 of the system 500 causes the computer processor 506 to initiate the operations of the plume arrival time display generation method 340.

Referring to FIG. 1, FIG. 2A, FIG. 2B, FIG. 3 and FIG. 5, at an operation initialize for display target 300, the data structure for display is initialized. This data can vary depending on the display target. For example when the display type is a graphics image it can include the display geometry, coordinate system, color depth, and other relevant display properties. This contrasts with a GIS data structure where the data could be in a georeferenced polygon encoded in an XML format. Examples of display targets include graphics displays, GIS-compatible data structures (KML, ESRI Shapefile), and raster image files (GeoTIFF, PNG, JPG).

Again referring to FIG. 1, FIG. 2A, FIG. 2B, FIG. 3 and FIG. 5, in accordance with the first exemplary embodiment, at an operation generate time contour lines 301, once the target has been specified, time contour lines are generated from the arrival time data structures. Time contour lines can be generated for any valid time within the simulation but a typical display will depict time contours with an increasing time interval (e.g. 5, 15, 30, and 60 minute arrival times). This process continues until all time contours have been calculated, according to the additional Time Contours? 302 operation decision diamond.

For the various components of the display, an intermediate data structure is generated that is then sent to the display target. For the case where the final display is a computer monitor, the data structure can be a raster image comprised of color information or a set of polygons that represent each element of the display. The data structures for each of the Plume Arrival elements are not exclusively raster or vector and can be of different times depending on the requirements of the display.

Referring again to FIG. 1, FIG. 2A, FIG. 2B, FIG. 3 and FIG. 5, and further in accordance with the first exemplary embodiment, these data structures are then composited with the Footprint forming the base layer by the composite footprint 303 operation.

Subsequently, the composite plume 304 operation composites plume contours.

And, at the composite time contour 305 operation, the arrival time contours are composited. The compositing operations can take place on the CPU (such as the computer processor 506, on dedicated graphical hardware or a mixture of the two.

Further, according to the first exemplary embodiment, and referring to FIG. 1, FIG. 2A, FIG. 2B, FIG. 3 and FIG. 5, multiple time contours are then processed and composited to the screen according to instructions at the Additional Time Contours?306 decision operation. A similar process is followed for GIS displays or raster files where the output is typically sent to a storage device or over a network connection for use by a separate program. For example sending a PNG image via an email attachment or viewing the Plume Arrival Time as an overlay in a GIS Program.

In a third exemplary embodiment, the operations of the plume arrival time operational use method 450 includes the following operations:

Referring again to FIG. 1, FIG. 2A, FIG. 2B, FIG. 3, FIG. 4 and FIG. 5, in accordance with the third exemplary embodiment, at An unknown contaminant has been released 400 operation, the program code of the method 450 executed by the computer processor 506 of the system 500 causes the computer processor 506 to initiate the multiple chemical sensors alarm 401 operation. In this third exemplary embodiment, a chlorine leak from a tanker in a railroad yard causes sensor(s) 570, downwind from the source 100, to activate an alarm:

Thus at a multiple chemical sensors alarm 401 operation, sensor(s) 570 activate an alarm indicating to the computer processor 510, communicatively over the network 572, that chlorine is detected.

Again referring to FIG. 1, FIG. 2A, FIG. 2B, FIG. 3, FIG. 4 and FIG. 5, in accordance with the third exemplary embodiment, at an operation initial estimate of source location 402, an operator trained in the use of CT-ANALYST uses the backtrack capability of CT-ANALYST to obtain a computer calculated estimate of the chlorine source location and then enters, using an input device 514, the source estimate location data into the computer processor 510, causing the source location estimate data to be available electronically (i.e., either as analog data or digital data) in memory 508 of the computer processor 510, for subsequent processing in plume arrival time calculation method 230 and/or in plume arrival time display generation method 340. Or, a subroutine or algorithm is called to execute CT-ANALYST backtrack routines to obtain an initial estimate of the location of the source 100, and then store the estimate in memory 508 of the computer processor 510, thus making the initial estimate of the location data of the source 100 available for further processing in association with operations of calculating actual and/or estimated plume arrival time(s) and plume displays.

Referring again to FIG. 1, FIG. 2A, FIG. 2B, FIG. 3, FIG. 4 and FIG. 5, in accordance with the third exemplary embodiment, at an operation calculate arrival time of plume 403, the plume arrival time calculation method 230 and/or in plume arrival time display generation method 340 are called and executed so as to be run as algorithmic routines and/or subroutines by the computer processor 506, in association with the execution of the calculate arrival time of plume 403 operation.

At the operation, 404, by looking at the display 502 and based on the results of the plume arrival time calculation method 230 and the plume arrival time display generation method 340 displayed on display 502, the user notes that for the given conditions, a nearby industrial park will be affected in 10 minutes and a commercial area that is heavily populated during the day will be affected within the hour.

At operation 405, and adhering to standard operating procedures (SOP), the operator uses reverse 911 to inform the industrial park and the commercial district to evacuate the area specifying the evacuation route to avoid the contaminant.

HAZMAT authorities and/or first responders are dispatched to look for the release and the HAZMAT responder personnel are directed (via communications capabilities of the computer processor 506 via the network 572 of system 500) to either wear protective gear if entering the hazard area or are directed to avoid the contaminated area completely. Or an algorithm is called to run an automated warning announcement, which is automatically transmitted to responders over the network 572.

Further according to the third exemplary embodiment, the operator and/or system, at Additional Information Arrived? 406 operation, receives a detailed report and/or report data from the railroad yard about the contaminant via network 572. The user and/or the computer processor 510 programmatically either updates the information about the source estimate at the refine source estimate 407 operation, or determines that the emergency is over at Emergency Over? 408 decision operation. If the emergency is over, then the plume arrival time operational use method 450 resets and/or returns to the Calculate Arrival Time of Plume 403 operation, where if there is no indication of a plume the system can reset and/or end. However, if there is indication of a plume resulting from the update operation in the Additional Information Arrived? 406 operation, then the system continues operations, until no more plumes are detected and the operations of 450 end.

When, a change in the hazard area is minor, the SOP continues by directing HAZMAT personnel to begin the process of stopping the leak and beginning cleanup. This process of refining the source estimate and following the SOP continues until the emergency has been mitigated as decided in operation Emergency Over? Operation 408.

While the exemplary embodiments have been particularly shown and described with reference to preferred embodiments thereof, it will be understood by those skilled in the art that the preferred embodiments including the first exemplary embodiment, and the second exemplary embodiment have been presented by way of example only, and not limitation; furthermore, various changes in form and details can be made therein without departing from the spirit and scope of the invention. Thus, the breadth and scope of the present exemplary embodiments should not be limited by any of the above described preferred exemplary embodiments, but should be defined only in accordance with the following claims and their equivalents. All references cited herein, including issued U.S. patents, or any other references, are each entirely incorporated by reference herein, including all data, tables, figures, and text presented in the cited references. Also, it is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The foregoing description of the specific embodiments will so fully reveal the general nature of the invention that others can, by applying knowledge within the ordinary skill of the art, readily modify and/or adapt for various applications such specific embodiments, without undue experimentation, and without departing from the general concept of the present invention. Therefore, such adaptations and modifications are intended to be within the meaning and range of equivalents of the disclosed embodiments claimed herein and below, based on the teaching and guidance presented herein and the claims which follow.

What is claimed is:

1. A method comprising:
   receiving at least one source location of an airborne contaminant in an area comprising an urban landscape;
   receiving a wind speed;
   receiving a wind direction; and
   generating a plurality of arrival time contours based on the at least one source location, the wind speed, and the wind direction.

2. The method according to claim 1, wherein the plurality of arrival time contours depicts an evolution of a hazard area footprint over time.

3. The method according to claim 2, wherein the at least one source location comprises at least one of at least one sensor location and at least one contaminant location.

4. The method according to claim 2, wherein said generating a plurality of arrival time contours based on the at least one source location, the wind speed, and the wind direction comprises accessing a nomograf database a single time, the nomograf database comprising right and left edges of a plume corresponding to a specific geographic location, wherein the wind speed operates on the right and left edges to produce the plurality of arrival time contours.

5. The method according to claim 4, further comprising:
   receiving a contaminant density and contaminant type; and
   generating a plurality of health effect contours based on the single-time accessing of the nomograf database, the contaminant density, and the contaminant type, the plurality of health effect contours depicting a plurality of health risks.

6. A method comprising:
   receiving at least one source location of an airborne contaminant in an area comprising an urban landscape;
   receiving a wind speed;
   receiving a wind direction; and
   receiving a contaminant density and contaminant type; and
   generating a plurality of health effect contours depicting a plurality of health risks based on the at least one source location, the wind speed, the wind direction, the contaminant density, and the contaminant type.

7. The method according to claim 6, wherein said generating a plurality of health effect contours depicting a plurality of health risks based on the at least one source location, the wind, the wind direction, the contaminant density, and the contaminant type comprises accessing a nomograf database a single time, the nomograf database comprising right and left edges of a plume corresponding to a specific geographic location, wherein the wind speed operates on the right and left edges to produce the plurality of health effect contours.

8. The method according to claim 6, wherein the at least one source location comprises at least one of at least one sensor location and at least one contaminant location.

* * * * *